(12) United States Patent
Peine et al.

(10) Patent No.: US 12,102,403 B2
(45) Date of Patent: Oct. 1, 2024

(54) ROBOTIC SURGICAL SYSTEMS WITH USER ENGAGEMENT MONITORING

(71) Applicant: Covidien LP, Mansfield, MA (US)

(72) Inventors: William J. Peine, Ashland, MA (US); Steven J. Levine, Framingham, MA (US); Albert Dvornik, Somerville, MA (US); Mantena V. Raju, Medford, MA (US); Chen Chen, Malden, MA (US)

(73) Assignee: Coviden LP, Mansfield, MA (US)

( * ) Notice: Subject to any disclaimer, the term of this patent is extended or adjusted under 35 U.S.C. 154(b) by 197 days.

(21) Appl. No.: 17/777,761

(22) PCT Filed: Dec. 17, 2019

(86) PCT No.: PCT/US2019/006735
§ 371 (c)(1),
(2) Date: May 18, 2022

(87) PCT Pub. No.: WO2021/126163
PCT Pub. Date: Jun. 24, 2021

(65) Prior Publication Data
US 2023/0010350 A1    Jan. 12, 2023

Related U.S. Application Data

(63) Continuation-in-part of application No. 16/966,666, filed as application No. PCT/US2019/016241 on Feb. 1, 2019.
(Continued)

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/74* (2016.02); *A61B 90/06* (2016.02);
(Continued)

(58) Field of Classification Search
CPC ................................ G06F 3/013; G06F 3/033
See application file for complete search history.

(56) References Cited

U.S. PATENT DOCUMENTS 6,132,368 A    10/2000  Cooper
6,206,903 B1    3/2001  Ramans
(Continued)

FOREIGN PATENT DOCUMENTS

JP    2019526315 A    9/2019
WO    2017100434 A1    6/2017
(Continued)

OTHER PUBLICATIONS

Extended European Search Report dated Aug. 21, 2023 for European Patent Application No. 19956887.4 (9 pages).
(Continued)

*Primary Examiner* — Joseph R Haley
(74) *Attorney, Agent, or Firm* — Carter, DeLuca & Farrell LLP

(57) ABSTRACT

A robotic surgical system with user engagement monitoring includes a surgeon console having a hand detection system and a tracking device including an image capture device configured to capture an image of a user position reference point, wherein information from the hand detection system and the tracking device are combined to control operation of the robotic surgical system.

19 Claims, 14 Drawing Sheets

Related U.S. Application Data

(60) Provisional application No. 62/625,714, filed on Feb. 2, 2018.

(51) Int. Cl.
*A61B 90/00* (2016.01)
*A61B 34/20* (2016.01)
*A61B 34/30* (2016.01)
*G06F 3/01* (2006.01)

(52) U.S. Cl.
CPC . *A61B 2034/2046* (2016.02); *A61B 2034/305* (2016.02); *G06F 3/013* (2013.01)

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |

(56) References Cited

U.S. PATENT DOCUMENTS

| | | |
|---|---|---|
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Arkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,426,561 B1 | 10/2019 | Kelly et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |

(56) References Cited

U.S. PATENT DOCUMENTS

| | | |
|---|---|---|
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,466,505 B1 * | 10/2022 | Schwartz ............... A61B 46/20 |
| 2013/0030571 A1 * | 1/2013 | Ruiz Morales ........ A61B 34/30 |
| | | 700/259 |
| 2014/0194897 A1 | 7/2014 | Kirschenman et al. |
| 2017/0042625 A1 | 2/2017 | Sartor |
| 2017/0312043 A1 * | 11/2017 | Ogawa ............... A61B 18/1445 |
| 2022/0382364 A1 * | 12/2022 | Verner .................... G06F 3/011 |

FOREIGN PATENT DOCUMENTS

| | | |
|---|---|---|
| WO | 2017210501 A1 | 12/2017 |
| WO | 2018179749 A1 | 10/2018 |
| WO | 2019050729 A1 | 3/2019 |
| WO | 2019099584 A1 | 5/2019 |
| WO | 2019152771 A1 | 8/2019 |

OTHER PUBLICATIONS

Chinese First Office Action dated Dec. 28, 2022 corresponding to counterpart Patent Application CN 1 202010490511.1.

International Search Report issued May 17, 2022 and Written Opinion completed Sep. 16, 2020 corresponding to counterpart Int'l Patent Application PCT/US2019/066735.

\* cited by examiner

ROBOTIC SURGICAL SYSTEMS WITH USER ENGAGEMENT MONITORING

CROSS-REFERENCE TO RELATED APPLICATIONS

The present application is a U.S. National Stage Application filed under 35 U.S.C. § 371(a) claiming the benefit of and priority to International Patent Application No. PCT/US2019/066735 filed on Dec. 17, 2019, the entire content of which being incorporated herein by reference.

The present application is also a Continuation-in-Part Application claiming the benefit of and priority to U.S. patent application Ser. No. 16/966,666, filed on Jul. 31, 2020, which is a U.S. National Stage Application filed under 35 U.S.C. § 371(a) claiming the benefit of and priority to International Patent Application Serial No. PCT/US2019/016241, filed on Feb. 1, 2019, which claims the benefit of and priority to U.S. Provisional Patent Application Ser. No. 62/625,714, filed on Feb. 2, 2018, the entire content of each of which being incorporated herein by reference.

BACKGROUND

Robotic surgical systems have grown in popularity, and the ergonomics and comfort in using robotic surgical systems have improved through an open-console architecture. In contrast to a closed-console architecture, which requires a surgeon to place her head within an immersive display apparatus to operate the robotic surgical system, an open-console architecture enables the surgeon to use the surgeon console while maintaining more open communication with other surgeons and staff in the operating room. The open-console architecture also enables the surgeon to be more aware of events occurring within the operating room and places the surgeon in a better position to handle emergency situations that may arise during the course of a surgical procedure.

With the open-console architecture, however, the surgeon may become distracted from engagement with the surgeon console more easily than they may be with a closed-console architecture. Further, systems need to be implemented such that the surgeon console is receiving and/or tracking information from the surgeon alone, or is capable of segregating information received and/or tracked which relates to the surgeon from information received and/or tracked which relates to other individuals in close proximity to the surgeon console. Robotic surgical systems having an open-console architecture, therefore, may carry increased safety risks. Accordingly, systems, devices, and methods are needed to mitigate safety risks stemming from surgeon distraction from engagement with robotic surgical systems.

SUMMARY

In one aspect, this disclosure describes a robotic surgical system with user engagement monitoring. The robotic surgical system includes a robot assembly, a surgeon console, and a tracking device. The robot assembly includes a robotic arm coupled to a surgical instrument. The surgeon console includes a handle and a display device. The handle is communicatively coupled to at least one of the robot assembly, the robotic arm, or the surgical instrument. The tracking device includes an image capture device configured to capture an image of a user position reference point. At least one of the surgeon console or the tracking device is configured to compute, based on the captured image, a position of the user position reference point relative to the display device; determine whether a user is engaged with or disengaged from the surgeon console based on the computed position; and, in response to a determination that the user is disengaged from the surgeon console, cause the robotic surgical system to operate in a safe mode.

In embodiments, at least one of the surgeon console or the tracking device is further configured to compute the position of the user position reference point by generating location data corresponding to at least one of the position, or an orientation, of the user position reference point, within a three dimensional coordinate space, relative to the display device.

In embodiments, in the determination of whether the user is engaged with or disengaged from the surgeon console, at least one of the surgeon console or the tracking device is further configured to compute a difference angle based on the position and orientation of the user position reference point relative to the display device; compare the difference angle to a first threshold angle; and, in response to a determination that the difference angle is greater than the first threshold angle, determine that the user is disengaged from the surgeon console.

In embodiments, at least one of the surgeon console or the tracking device is further configured to select the first threshold angle from a plurality of first threshold angles based on the position and the orientation of the user position reference point relative to the display device.

In embodiments, at least one of the surgeon console or the tracking device is further configured to compute, based on the position and the orientation of the user position reference point, a direction of movement of the user position reference point relative to the display device; and select the first threshold angle based on the direction of movement of the user position reference point.

In embodiments, in the determination of whether the user is engaged with or disengaged from the surgeon console, at least one of the surgeon console or the tracking device is further configured to, in response to a determination that the difference angle is less than the first threshold angle, determine whether the difference angle is less than a second threshold angle that is smaller than the first threshold angle; and, in response to a determination that the difference angle is less than the second threshold angle, determine that the user is engaged with the surgeon console.

In embodiments, at least one of the surgeon console or the tracking device is further configured to, in response to the determination that the user is engaged with the surgeon console, cause the robotic surgical system to exit the safe mode.

In embodiments, at least one of the surgeon console or the tracking device is further configured to, at a time when the robotic surgical system operates in the safe mode and in response to a determination that the user is engaged with the surgeon console, cause the robotic surgical system to exit the safe mode after an elapsing of a threshold amount of time after the determination that the user is engaged.

In embodiments, the robotic surgical system further comprises a computing device. At least one of the surgeon console or the tracking device is further configured to, at a time when the robotic surgical system operates in the safe mode, restrict movement of the handle from a previous position of the handle; and transmit, to the computing device, instructions to restrict movement of at least one of the robot assembly, the robotic arm, or the surgical instrument. The computing device is configured to receive the instructions and transmit the instructions to at least one of the robot assembly, the robotic arm, or the surgical instrument. At least one of the robotic arm, the robot assembly, or the surgical instrument is configured to receive the instructions, and restrict movement of at least one of the robot assembly, the robotic arm, or the surgical instrument in response to the instructions.

In embodiments, at least one of the surgeon console or the tracking device is further configured to, at a time when the robotic surgical system operates in the safe mode, prevent a movement of the handle from causing a corresponding movement of the robotic arm communicatively coupled to the handle.

In embodiments, at least one of the surgeon console or the tracking device is further configured to detect an amount of movement of the handle; determine, based on the amount of movement of the handle, an amount of movement of at least one of the robot assembly, the robotic arm, or the surgical instrument to be caused in response to the movement of the handle; and cause at least one of the robot assembly, the robotic arm, or the surgical instrument to move by the determined amount of movement. At a time when the robotic surgical system operates in the safe mode, the determination of the amount of movement of at least one of the robot assembly, the robotic arm, or the surgical instrument to be caused includes applying a downward scaling factor.

In embodiments, at least one of the surgeon console or the tracking device is further configured to compute a velocity of a movement of the handle and modify the downward scaling factor based on the velocity.

In embodiments, the surgeon console includes a plurality of motors corresponding to the handle, each of the motors being operably coupled to the handle and being associated with a direction of movement of the handle. At a time when the robotic surgical system operates in the safe mode, at least one of the surgeon console or the tracking device is further configured to compute a velocity of a movement of the handle; compute a direction of the movement of the handle; compute, based on the velocity of the movement of the handle, a force in a direction opposite to the direction of the movement of the handle; identify, among the plurality of motors of the handle, a motor associated with the direction opposite to the direction of the movement of the handle; and cause actuation of the identified motor in the direction opposite to the direction of the movement of the handle to generate the computed force in the direction opposite to the direction of the movement of the handle.

In embodiments, the surgeon console further comprises a plurality of motors operably coupled to the handle and associated with a plurality of directions, respectively, of movement of the handle. At least one of the surgeon console or the tracking device is further configured to, in response to the determination that the user is disengaged with the surgeon console, identify a first position of the handle; compute a distance traveled by the handle from the first position of the handle; compute a direction of the movement of the handle; compute, based on the distance, a force in a direction opposite to the direction of the movement of the handle; identify, among the plurality of motors of the handle, a motor associated with the direction opposite to the direction of the movement of the handle; and cause actuation of the identified motor in the direction opposite to the direction of the movement of the handle to generate the computed force in the direction opposite to the direction of the movement of the handle.

In embodiments, the surgeon console is further configured to actuate the motor in the direction opposite to the direction of the movement of the handle until the handle is positioned in the first position.

In embodiments, the robotic surgical system further comprises eyewear including a plurality of markers, and the user position reference point includes at least one of the plurality of markers.

In embodiments, the user position reference point includes at least one of an eye, a head, or another portion of the user.

In embodiments, the display device is an autostereoscopic display device.

According to another aspect, the present disclosure describes another robotic surgical system with user engagement monitoring. The robotic surgical system includes a robot assembly and a surgeon console. The robot assembly includes a robotic arm coupled to a surgical instrument. The surgeon console includes a handle communicatively coupled to at least one of the robot assembly, the robotic arm, or the surgical instrument. The handle includes at least one of a capacitive sensor or an optical sensor. The surgeon console is configured to receive, from at least one of the capacitive sensor or the optical sensor, data related to contact with the handle by a user; determine, based on the data related to contact with the handle, whether the user is engaged with or disengaged from the surgeon console; and, in response to a determination that the user is disengaged from the surgeon console, cause the robotic surgical system to operate in a safe mode.

In embodiments, the surgeon console is further configured to, in the determination of whether the user is disengaged from the surgeon console, determine that the user is disengaged from the surgeon console in response to the data related to the contact with the handle indicating that the user is not in contact with the handle.

According to another aspect of the present disclosure, a robotic surgical system with user engagement monitoring includes a surgeon console having a hand detection system and a tracking device including an image capture device configured to capture an image of a user position reference point, wherein information from the hand detection system and the tracking device are combined to control operation of the robotic surgical system.

The robotic surgical system with user engagement monitoring includes a robot assembly including a robotic arm coupled to a surgical instrument; a surgeon console, and a tracking device. The surgeon console includes a handle assembly communicatively coupled to at least one of the robot assembly, the robotic arm, or the surgical instrument, the handle assembly including a body portion having a proximal end portion and a distal end portion, the body portion including a first actuator movable between an open position and a closed position. The surgeon console also includes a hand detection system including a first sensor disposed within the first actuator of the handle assembly for detecting finger presence on the first actuator, a second sensor disposed on the proximal end portion of the handle assembly for detecting palm presence about the proximal end portion, and an encoder disposed within the body portion of the handle assembly for detecting position of the first actuator relative to the body portion. The surgeon console further includes a display device; and a processing unit electrically coupled to the first, second, and third sensors for receiving and processing data from the first, second, and third sensors.

The tracking device includes an image capture device configured to capture an image of a user position reference point.

At least one of the surgeon console, the hand detection system or the tracking device is configured to compute, based on the captured image, a position of the user position reference point relative to the display device, determine whether a user is engaged with or disengaged from the surgeon console based on the computed position, determine whether a hand of the user is engaged with or disengaged from at least one of the first, second or third sensors of the hand detection system, and, in response to a determination that the user is disengaged from the surgeon console or the hand of the user is disengaged from at least one of the first, second or third sensors of the hand detection system, cause the robotic surgical system to operate in a safe mode.

At least one of the surgeon console, the hand detection system or the tracking device may be further configured to compute the position of the user position reference point by generating location data corresponding to at least one of the position, or an orientation, of the user position reference point, within a three-dimensional coordinate space, relative to the display device.

At least one of the surgeon console, the hand detection system or the tracking device may be further configured to, at a time when the robotic surgical system operates in the safe mode, in response to a determination that the user is engaged with the surgeon console by at least one of the tracking device or the hand detection system, cause the robotic surgical system to exit the safe mode after an elapsing of a threshold amount of time after the determination that the user is engaged.

The robotic surgical system may further include a computing device. At least one of the surgeon console, the hand detection system or the tracking device may be further configured to, at a time when the robotic surgical system operates in the safe mode, restrict movement of the handle assembly from a previous position of the handle assembly, and transmit, to the computing device, instructions to restrict movement of at least one of the robot assembly, the robotic arm, or the surgical instrument. The computing device may be configured to receive the instructions, and transmit the instructions to at least one of the robot assembly, the robotic arm, or the surgical instrument. At least one of the robotic arm, the robot assembly, or the surgical instrument may be configured to receive the instructions, and restrict movement of at least one of the robot assembly, the robotic arm, or the surgical instrument in response to the instructions.

At least one of the surgeon console, the hand detection system or the tracking device may be further configured to, at a time when the robotic surgical system operates in the safe mode, prevent a movement of the handle assembly from causing a corresponding movement of the robotic arm communicatively coupled to the handle assembly.

At least one of the surgeon console, the hand detection system or the tracking device may be further configured to detect an amount of movement of the handle assembly; determine, based on the amount of movement of the handle assembly, an amount of movement of at least one of the robot assembly, the robotic arm, or the surgical instrument to be caused in response to the movement of the handle assembly; and cause at least one of the robot assembly, the robotic arm, or the surgical instrument to move by the determined amount of movement. At a time when the robotic surgical system operates in the safe mode, the determination of the amount of movement of at least one of the robot assembly, the robotic arm, or the surgical instrument to be caused may include applying a downward scaling factor.

At least one of the surgeon console, the hand detection system or the tracking device may be further configured to compute a velocity of a movement of the handle assembly; and modify the downward scaling factor based on the velocity.

The robotic surgical system may further include a plurality of eyewear each including a discrete plurality of markers, wherein a first user position reference point includes first data from a first plurality of markers of first eyewear corresponding to the user, and a second user positioning reference point including second date from a second plurality of markers of second eyewear, different from the first data, corresponding to a non-user.

The first sensor may be a capacitive sensor, the second sensor may be an infrared sensor, and the third sensor may be an encoder.

In operation, when the hand detection system is in an initialization state, the hand detection system may utilize data from only the first and third sensors, and when the hand detection system is in an operation stage, the hand detection system may utilize data from the first, second, and third sensors.

In operation, when the hand detection system is in an initialization stage, the first actuator may move through a full range of motion between the open and closed positions, and the first sensor detects a capacitance value at each of a plurality of points through the full range of motion and the third sensor generates an encoder count at each of the plurality of points.

The hand detection system may include a lookup table including a baseline curve of the capacitance values as a function of the encoder counts and a calibrated curve of threshold capacitance values as a function of the encoder counts.

In operation, when the hand detection system is in an operation stage, the first sensor may detect a real-time capacitance value and the third sensor detects a real-time encoder count, and the real-time capacitance value and the real-time encoder count are compared to the lookup table to identify a positive or negative finger presence state of the handle assembly.

In operation, when the hand detection system is in an operation stage, the second sensor may detect a real-time value which is compared to a threshold value to identify a positive or negative palm presence state of the handle assembly.

The surgical instrument may be a jaw assembly including opposed jaw members, and when the first actuator is in the open position, the jaw members are in an open configuration, and when the first actuator is in the closed position, the jaw members are in a closed configuration.

The tracking device may monitor gestures of a head of the user and may combine data regarding the head gestures with data regarding a movement of the handle assembly to effectuate control of the surgical instrument.

The surgical instrument may be an endoscope.

The data regarding the head gestures monitored by the tracking system may be communicated to the endoscope to control a zoom scale, roll, pitch or yaw of an image captured by the endoscope.

The robotic surgical system may further include a wireless identification device wearable by the user to recognize engagement by the user or surgeon with the surgeon console. The wireless identification device may include at least one of identification information related to the user; robotic surgical system performance characteristic associated with the user; or proximity information of the wireless identification device relative to the surgeon console and/or the handle assembly.

The wireless identification device may be used in combination with the hand detection system for determining an awareness of the user.

BRIEF DESCRIPTION OF THE DRAWINGS

Various aspects and features of robotic surgical systems and methods of the present disclosure are described herein below with references to the drawings, wherein:

FIG. 12 is a top, perspective view, with parts removed, of the handle assembly of

FIG. 10;

DETAILED DESCRIPTION

Figure 1A:
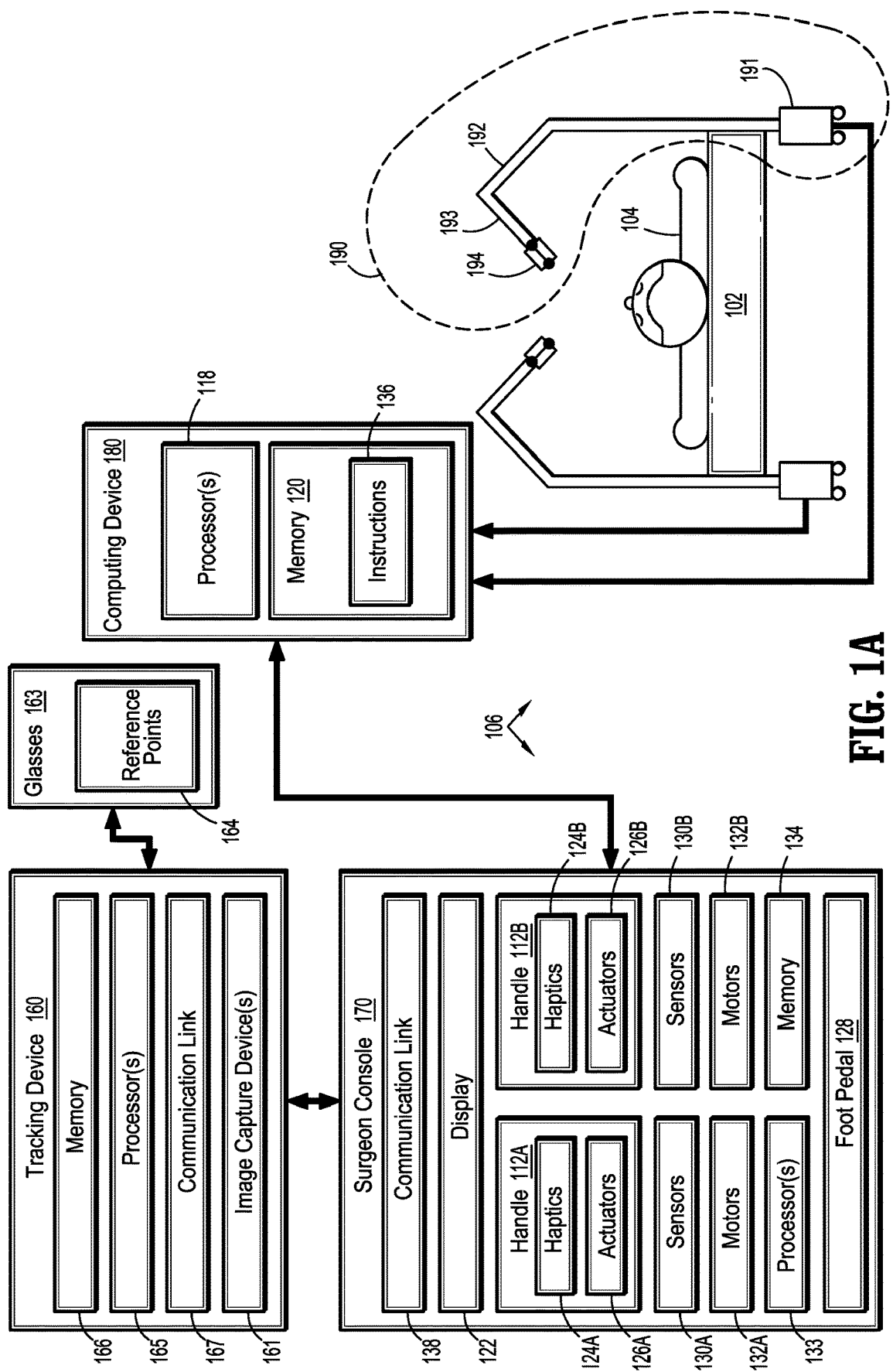
FIG. 1A illustrates an exemplary robotic surgical system, in accordance with an illustrative embodiment herein.

The present disclosure is directed to robotic surgical systems, devices, methods, and computer-readable media that mitigate safety risks stemming from surgeon distraction from engagement with robotic surgical systems during surgical robotic procedures. More particularly, the present disclosure relates to systems and methods for identifying disengagement of a user using the robotic surgical system and causing the robotic surgical system to operate in one or more safe modes when the user is disengaged, thereby mitigating the risk that the user unintentionally injures the patient or otherwise compromises the surgical procedure by actuating the robotic surgical system while distracted. The systems and methods described herein provide various techniques for tracking a user position relative to a display of a surgeon console and, based on the tracked user position, determining whether the user is disengaged from a surgeon console, even for open-console architectures. If the user is disengaged from the surgeon console, the robotic surgical system is operated in one or more safe modes. Utilizing the technologies, techniques, and embodiments described herein, users are provided with a safer operating environment in which to perform robotic surgeries, and patients are afforded a safer environment in which to receive surgical treatment via robotic surgical systems.

Embodiments of the present disclosure are now described in detail with reference to the drawings in which like reference numerals designate identical or corresponding elements in each of the several views. As used herein, the terms "user" and "clinician" refer to a doctor, a surgeon, a nurse, technician, medical assistant, or similar support personnel or any other person that may use the robotic surgical systems described herein. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Throughout this description, the term "proximal" refers to a portion of a system, device, or component thereof that is closer to a hand of a clinician, and the term "distal" refers to a portion of the system, device, or component thereof that is farther from the hand of the clinician.

The terms "artificial intelligence," "data models," or "machine learning" may include, but are not limited to, neural networks, convolutional neural networks (CNN), recurrent neural networks (RNN), generative adversarial networks (GAN), Bayesian Regression, Naive Bayes, nearest neighbors, least squares, means, and support vector regression, among other data science and artificial science techniques.

FIG. 1A shows an example robotic surgical system 100 in accordance with an exemplary embodiment herein. In general, the surgical system 100 is configured to determine whether or not a user is engaged with a surgeon console of the surgical system 100 and, based on that determination, operate in one of various operational modes in which the system is configured to operate, including one or more safe modes and one or more non-safe modes, which are also referred to as normal modes. As shown in FIG. 6 and described below, the types of safe modes in which the system 100 is configured to operate include, but are not limited to (1) a safe mode based on locking a handle and a robot assembly of the surgical system 100, (2) a safe mode based on preventing handle movement from causing corresponding robot assembly movement, (3) a safe mode based on a velocity of handle movement, (4) a safe mode based on handle velocity-based opposing force, and (5) a safe mode based on position-based opposing force. Additional details of determining whether a user is engaged with, or disengaged from, the robotic surgical system 100 and, in response, causing the surgical system 100 to operate in non-safe modes or safe modes are provided herein in the context of FIGS. 2 through 7. The specific number of components of the system 100 depicted in FIG. 1A and the arrangement and configuration thereof are provided for illustrative purposes only, and should not be construed as limiting. For instance, various embodiments herein employ fewer or greater than all of the components shown in FIG. 1A. Additionally, the system 100 depicted in FIG. 1A is provided as an illustrative context in which various exemplary embodiments herein are applicable.

The system 100 includes an operating table 102 upon which a patient 104 lies during a surgical procedure, a tracking device 160, a surgeon console 170 with which a user interacts during the surgical procedure, a computing device 180, and one or more robot assemblies 190. The tracking device 160, and the computing device 180 are communicatively coupled to one another and the one or more robot assemblies 190 by way of communication paths 106, which, in various embodiments herein, may be implemented as wired communication paths and/or as wireless communication paths.

Each of the one or more robot assemblies 190 includes multiple subunits 191, 192, 193, and 194. The subunit 191 is a cart unit, the subunit 192 is a setup arm unit, the subunit 193 is a robot arm unit, and the subunit 194 is an instrument drive unit. The subunits 191, 192, 193, 194, are operably coupled to each other directly or indirectly, and communicatively coupled to each other directly or indirectly by way of one or more communication paths (not shown in FIG. 1A). The cart unit 191 is arranged adjacent to the operating table 102 within range of the patient 104 undergoing the surgical procedure and is configured to move along side of the operating table 102 or the patient 104 and towards and away from the operating table 102 or the patient 104. The instrument drive unit 194 is couplable to one or more corresponding surgical instruments (not shown in FIG. 1A), and/or image capture devices (not shown in FIG. 1A) that may be interchangeably fastened thereto depending on the particular surgical procedure being performed. Exemplary types of surgical instruments include, but are not limited to, a probe, an end effector, a grasper, a knife, scissors, and/or the like. Exemplary types of the image capture devices include, but are not limited to, endoscopic cameras, laparoscopic cameras, any type of image capture apparatuses, or instruments coupled to image capture apparatuses.

The computing device 180 includes one or more processors 118 and one or more memory units 120, and the one or more processors 118 are operably coupled to the one or more memory units 120. In various embodiments, the computing device 180 may be integrated with the surgeon console 170, or may be a standalone device, such as a computing tower, disposed within or near the operating room. The one or more processors 118 may be any type of suitable processor that is adapted to perform or execute the techniques or operations or instructions described herein. The one or more memory units 120 store instructions, such as instructions 136 (in an example, software), to be executed by the one or more processors 118, and the techniques described herein are performed by the computing device 180 in response to the one or more processors 118 executing the instructions stored in the one or more memory units 120. The one or more memory units 120 may be any type of hardware device suitable to store machine instructions, data, and/or the like.

The surgeon console 170 includes a communication link 138, a display device 122, one or more handles 112A, 112B (collectively, handle(s) 112), one or more processors 133, one or more memory units 134, a foot pedal 128, and at least one motor corresponding to directions in which the handle 112 is configured to move, such as motors 132A for handle 112A and motors 132B for handles 112B. The display device 122 may be a touch display, or include a touch screen, which is configured to receive inputs via a user's touch. In some embodiments, the display device 122 is configured to display a graphical user interface (GUI) configured to receive inputs for various settings of the surgical system 100 including, but not limited to, settings for safe modes and threshold data used in determining whether a user is disengaged with the. The display device 122 may be configured to display images received by the surgeon console 170, including images related to the surgical site on or within the patient 104 from an image capture device coupled to the robot assembly 190. In some embodiments, the display device 122 is a two-dimensional (2D) display device. In some embodiments, the display device 122 is configured to display one or more stereoscopic images received by the surgeon console 170 to allow a user to view the one or more stereoscopic images as three-dimensional (3D) images. In some embodiments, the display device 122 is an autostereoscopic display device.

The user interacts with the surgeon console 170 using the handles 112 during a surgical procedure. In some embodiments, the handle 112A is a left handle and the handle 112B is a right handle, operated upon by a left hand and right hand, respectively, of the user. The handle 112A, in some embodiments, includes various haptics 124A and/or actuators 126A, which provide feedback to the user relating to various tissue parameters or conditions, such as, tissue resistance due to manipulation, cutting, or otherwise treating, pressure by the instrument onto the tissue, tissue temperature, tissue impedance, and/or the like. Similarly, the handle 112B, in some embodiments, includes various haptics 124B and/or actuators 126B, which are configured similar to as haptics 124A and/or actuators 126A. The haptics 124A and 124B are referred to herein collectively as haptics 124. The actuators 126A and 126B are referred to herein as collectively as the actuators 126. As can be appreciated, such haptics 124 provide the surgeon with enhanced tactile feedback simulating actual operating conditions. The haptics 124 may include vibratory motors, electroactive polymers, piezoelectric devices, electrostatic devices, subsonic audio wave surface actuation devices, reverse-electrovibration, or any other device capable of providing a tactile feedback to a user. As mentioned above, the handles 112 may also include a variety of different actuators 126, which, for instance, may be employed for delicate tissue manipulation and/or treatment further enhancing the surgeon's ability to mimic actual operating conditions.

The surgeon console 170 includes one or more sensors 130A and 130B (collectively, 130) that are operably coupled to a handle 112. For example, the sensors 130A may be operably coupled to the handle 112A and the sensors 130B may be operably coupled to the handle 112B. One or more of the sensors 130A and 130B may be configured to determine metrics related to the motions of the handles to which they are operably coupled. Exemplary types of the metrics related to the motions of the handles 112 include, but are not limited to, a direction of movement of the handles 112, a velocity of movement of the handles 112, a distance of movement of the handles 112, and/or the like. In some embodiments, the transmits the metrics data related to the motions of the handles 112 to the computing device 180 and/or robot assemblies of the surgical system 100, such as the robot assembly 190. One or more of the sensors 130A and 130B may be a capacitive sensor and/or an optical sensor and the may be configured to determine whether a user is in contact with the handle 112A or the handle 112B based on the data received from the capacitive sensors and/or the optical sensors of the sensors 130A and 130B.

Each of the handles 112 is operably coupled to and associated with at least one motor for each direction of movement in which the handle 112 is configured to move. Examples of such motors are motors 132A and motors 132B (collectively, motors 132) for the handle 112A and the handle 112B, respectively. Each motor of motors 132A is operably coupled to the handle 112A and each motor of the motors 132A is associated with a direction of movement in which the handle 112A is configured to move. Similarly, each motor of motors 132B is operably coupled to handle 112B and each motor of the motors 132B is associated with a direction of movement in which the handle 112B is configured to move. Each motor of the motors 132 associated with a direction is configured to actuate in the associated direction to cause movement of the handle 112 in the associated direction, and to actuate in a direction opposite to their associated direction to resist the movement of the handle 112 in the associated direction. For example, if handle 112A is configured to move in a left direction then at least one motor of the motors 132A is associated with the left direction. If it is desired that the handle 112A should be moved in the left direction, then the actuates the motor associated with the left direction in a direction that corresponds to the left direction in order to assist in the movement of the handle 112A in the left direction, and if it is desired that the movement of the handle 112A in the left direction should be resisted, then the actuates the motor associated with the left direction in a direction that corresponds to a direction opposite to the left direction in order to resist the movement of the handle 112A in the left direction. The motors 132 are configured to be actuated at various speeds.

The foot pedal 128 is configured to receive one or more inputs from a user to the surgeon console 170. The foot pedal 128 is configured to be placed into two or more positions and a position of the foot pedal 128 is associated with an input to the surgeon console 170. The selection of a position of the foot pedal 128 provides the associated input to the surgeon console 170. In some embodiments, users provide inputs to update settings and/or configuration data related to one or more components of the surgical system 100 using the foot pedal 128. The is configured to update settings and/or configuration data based on the inputs received via the foot pedal 128, and transmit the updated settings and/or configuration data to the computing device 180 and/or the one or more robot assemblies, such as the robot assembly 190. In some embodiments, one of the positions of the foot pedal 128 is configured to be a rest position of the foot pedal 128, and an input signal that indicates that the foot pedal 128 is in the rest position is transmitted to the when the foot pedal 128 is in the rest position. In some embodiments, the foot pedal 128 is a momentary foot pedal switch and inputs to the surgeon console 170 are transmitted based on a sequence of interrogations with the foot pedal 128, such as double tapping the foot pedal 128. The surgeon console 170 transmits the inputs received via the foot pedal 128 to the computing device 180 and/or the robot assemblies of the surgical system 100, such as robot assembly 190.

Although FIG. 1A shows the tracking device 160 and the surgeon console 170 as being separate components communicatively coupled to one another via communication paths and the communication links 138, 167, this configuration is merely provided as an illustrative example. In other embodiments, the tracking device 160 is integrated into the surgeon console 170. Accordingly, functionality described herein as being performed by the tracking device 160 and/or by the surgeon console 170 may, in various other embodiments, be performed by the tracking device 160, by the surgeon console 170, by any combination thereof, and/or by any combination of components thereof, such as the processors 133 or 165 and/or memories 134 or 166. According to another embodiment, as will be described in greater detail below, the functionality of the tracking device 160 may be supplemented with the functionality of a hand detection system for handle assemblies 1000 (see FIGS. 9-11) of the surgeon console 170.

Figure 1B:
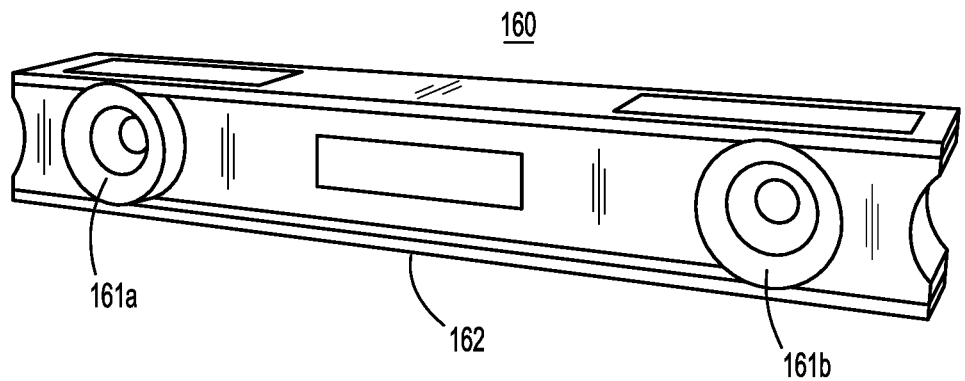
FIGS. 1B and 1C illustrate an exemplary optical tracking device of the robotic surgical system of FIG. 1.

In one embodiment, the tracking device 160 includes one or more image capture devices 161, one or more processors 165, one or more memories 166, and one or more communication links 167. The surgeon console 170 is configured to, in real-time or near real-time, identify and track a user position reference point (for example, a portion of a user or of eyewear 163 worn by the user); determine whether the user is engaged with, or disengaged from, the; and cause the surgical system 100 to operate in a non-safe mode or a safe mode based on a result of the determination. As used herein, the term user position reference point generally refers to at least a portion of the user and/or at least a portion of an object (such as eyeglasses) that the surgeon console 170 can utilize as a basis upon which to compute and/or track a position and/or an orientation of the user relative to a reference coordinate system, such as a coordinate system defined by a front plane of the display device 122 facing the user. In various embodiments, the user position reference point may include a single portion of the user or the object or include multiple portions of the user or the object. As used herein in this context, the term "a portion of a user" refers to any anatomical part of a user, including but not limited to, an eye, a pupil within an eye, a head, a face, and/or the like. Exemplary types of the one or more image capture devices 161 are image capture devices 161a and 161b, illustrated in FIG. 1B. As shown in FIG. 1B, the image capture devices 161a and 161b are positioned apart from each other. The is configured to cause the image capture devices 161 to move to track the user portion reference point over one or more time periods. In some embodiments, the one or more image capture devices 161 are housed within a housing unit, such as housing unit 162, and the housing unit 162 is included within or attached to the.

Figure 1C:
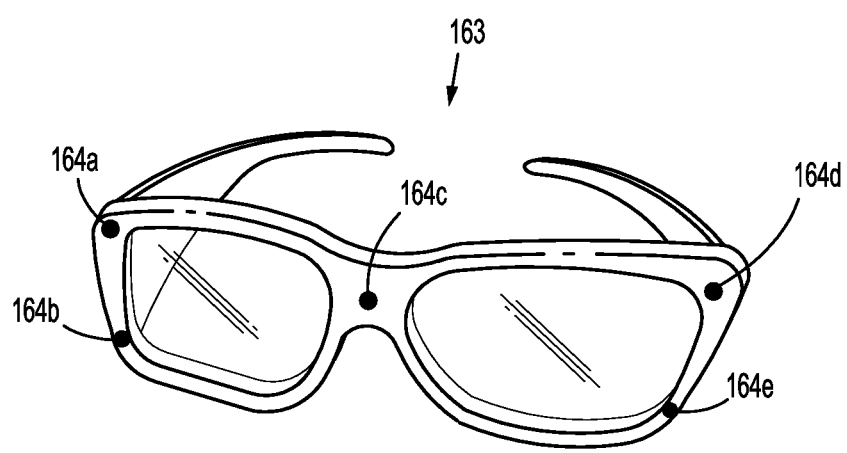

In some embodiments, the is trained on one or more facial and/or feature recognition algorithms and is configured to detect eyes, pupils, a head, a face, and/or the like of a user by applying the one or more facial and/or feature recognition algorithms on one or more images captured by the image capturing devices 161. In some embodiments, the surgeon console 170 is configured to perform optical tracking of the user position reference point, and the one or more image capture devices 161 are equipped with infrared (IR) pass filters (not shown in FIGS. 1A-1C) in front of their lenses and a ring of IR light emitting diodes (LEDs) (not shown in FIGS. 1A-1C) around the lens. In optically tracking the user position reference point, the surgeon console 170 periodically illuminates a desired space with IR light using the IR LEDs, and identifies and tracks a the user position reference point by detecting the IR light reflections from markers placed on a portion of the user or on an object, such as the eyewear 163, worn by the user, using the one or more image capture devices 161. An exemplary type of the eyewear 163 including markers 164a, 164b, 164c, 164d, 164e, (collectively, 164), which may be reflective markers, positioned thereon is illustrated in FIG. 1C.

The surgeon console 170 includes one or more processors 133 and one or more memory units 134. The one or more processors 133 are operably coupled to the one or more memory units 134. The one or more processors 133 may be any type of suitable processor that is adapted to perform or execute the techniques or operations or instructions described herein. The one or more memory units 134 store instructions (not shown in FIG. 1A) to be executed by the one or more processors 133, and the techniques described herein may be performed by the in response to the one or more processors 133 executing the instructions stored in the one or more memory units 134. The one or more memory units 134 may be any type of hardware device suitable to store machine instructions, data, and/or the like.

The processors 118, 133, 165 and the processors (not shown in FIG. 1A) of the robot assemblies 190 (collectively, processors of the surgical system 100) may be hardware processors programmed to perform the techniques described herein pursuant to the instructions in firmware, memory, or other storage, or a combination thereof. Similarly, the processors of the surgical system 100 may also be one or more application specific integrated circuits (ASICs), field programmable gate arrays (FPGAs) that are persistently programmed to perform the techniques or operations described herein. The processors of surgical system 100 may also be a central processing unit (CPU), a digital signal processor (DSP), a microprocessor, or any other device that incorporates hard wired logic or program logic or both to perform the operations or techniques described herein.

The memory units 120, 134, 166 and the memory units (not shown in FIG. 1A) of the robot assemblies 190 (collectively, memory units of the robotic surgical system 100) may be volatile memory, such as random access memory (RAM) (e.g., dynamic random access memory (DRAM), static random access memory (SRAM), and/or the like). The memory units of robotic surgical system 100 may be non-volatile memory, such as read-only memory (ROM) (e.g., programmable read-only memory (EPROM), electrically erasable programmable read-only memory (EEPROM), non-volatile RAM (NVRAM), and/or the like). The memory units of the surgical system 100 may also be magnetic, optical, or electrical media. As will be appreciated, the processors and the memory units of the robotic surgical system 100 implementation is provided by way of example only, and should not be construed as limiting. For instance, procedures of any of the embodiments of the present disclosure may be implemented by hardware components, firmware components, software components, and/or any combination thereof.

Figure 2A:
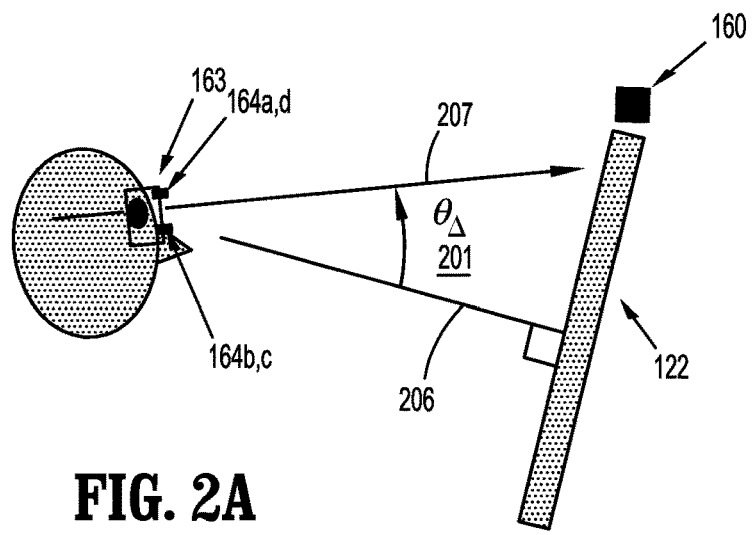
FIGS. 2A-2C illustrate exemplary aspects of how the robotic surgical system of FIG. 1 may be used to monitor user engagement.

Turning now to FIG. 2A, an exemplary arrangement of the display device 122 and the one or more image capture devices 161 is shown in accordance with one or more embodiments herein. The one or more image capture devices 161 are positionally affixed to the display device 122 such that the positional relationship between the image capture devices 161 and the display device 122 is known, and the surgeon console 170, the tracking device 160, and/or the computing device 180 are configured to determine whether a user is engaged with, or disengaged from, the surgeon console 170 based in part on the positional relationship between the image capture devices 161 and the display device 122. In some embodiments, the positional relationship between the image capture devices 161 and the display device 122 is provided as an input to the surgeon console 170, for example, by a user. The may be configured to compute the positional relationship between the one or more image capture devices 161 and the display device 122, based on the orientation of the display device 122 relative to a fixed location of the environment in which the surgeon console 170 is placed, such as the ground or floor of a room.

In tracking the user position reference point in real-time and over one or more time periods, the surgeon console 170 computes a location of the user position reference point relative to the display device 122 in each of the time periods. The location of the user position reference point relative to the display device 122 is computed based in part on data related to the positional relationship between the one or more image capture devices 161 and the display device 122. In computing the location of the user position reference point relative to the display device 122, the surgeon console 170 computes a position and an orientation of the user position reference point. The position of the user position reference point is computed in a three-dimensional coordinate space, for example, in an x, y, and z coordinate space, and the orientation of the user position reference point is computed by computing the roll, pitch, and yaw angles of the user position reference point. The position and the orientation of the user position reference point are computed relative to the display device 122.

Figure 2B:
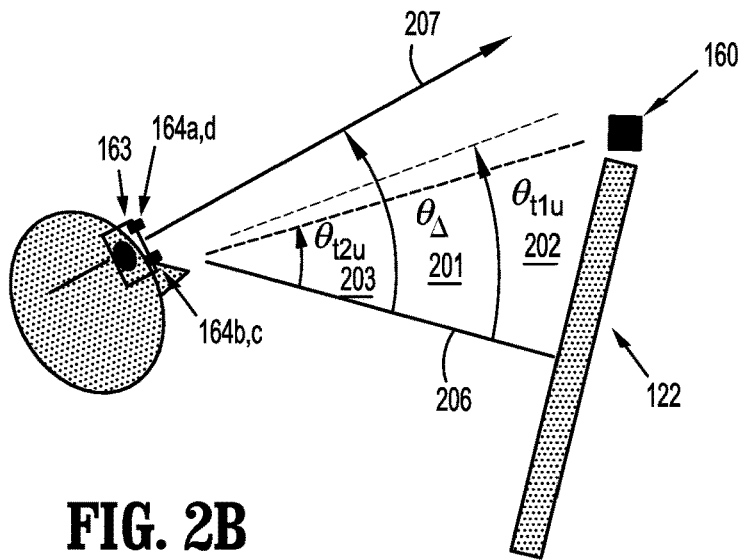
Figure 2C:
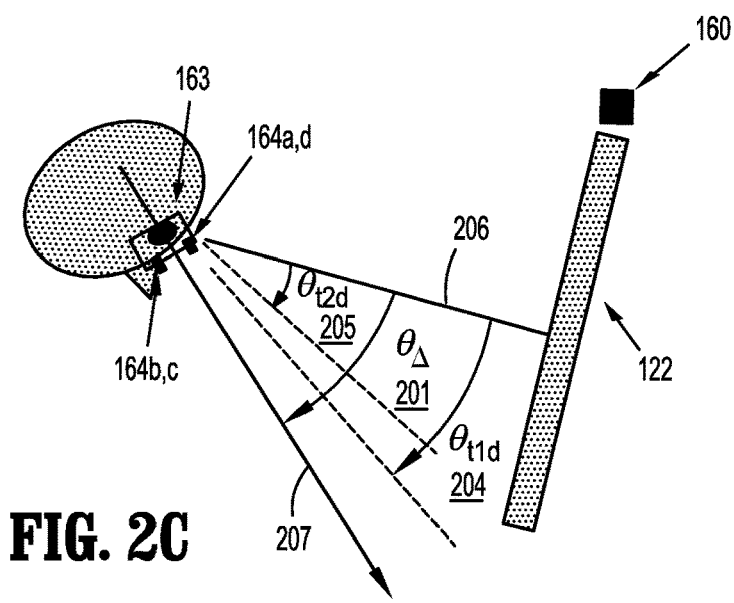

Using the position and the orientation of the user position reference point, the surgeon console 170 computes a difference angle $\theta_A$. As used herein, the term "difference angle" is an angle between an imaginary line 206 normal or perpendicular to a front plane of the display device 122 and an imaginary line 207 normal to a plane formed by user position reference point(s) (for example, three user position reference points corresponding to three of the markers 164) being tracked. An example of such a difference angle $\theta_A$ is shown as difference angle $\theta_A$ 201 in FIG. 2A. The normal imaginary line 207 is substantially aligned with a direction in which the surgeon is looking. In the example of FIG. 2A, FIG. 2B, FIG. 2C, a user is wearing the eyewear 163, which has the markers 164 positioned thereon, at least three markers 164 of which represents the user position reference points, and the is performing optical tracking of the user position reference points. The surgeon console 170 computes the difference angle $\theta_A$ 201 by computing a relative angle between the imaginary line 207 normal to the plane formed by the markers 164 and the imaginary line 206 normal to the front plane of the display device 122.

As the user's head moves, the position of the imaginary line 207 normal to the plane formed by the markers 164 changes from a first position (for example, the position shown in FIG. 2A) to a second position (for example, the positions shown in FIG. 2A or FIG. 2B), and accordingly the difference angle $\theta_A$ 201 changes, as shown in FIG. 2B and FIG. 2C. In embodiments where the surgeon console 170 is tracking the user position reference points by detecting features of the user, such as the eyes of the user, the surgeon console 170 computes the difference angle $\theta_A$ 201 by computing a position of an imaginary line (not shown in FIGS. 2A-2C) normal to the detected features of the user and a position of the imaginary line 206 normal to the front plane of the display device 122, and by computing an angle between the computed positions of the two imaginary lines. As the detected features move relative to the display device 122, the position of the imaginary line normal to the detected features changes and the difference angle $\theta_A$ 201 changes accordingly.

The is configured to determine whether the user is engaged with, or disengaged from, the surgeon console based in part on the difference angle $\theta_A$ 201. Additional details of the determination by the as to whether the user is engaged with, or disengaged from, the surgeon console 170 are provided herein in the contexts of FIG. 3, FIG. 4, and FIG. 5.

Figure 3:
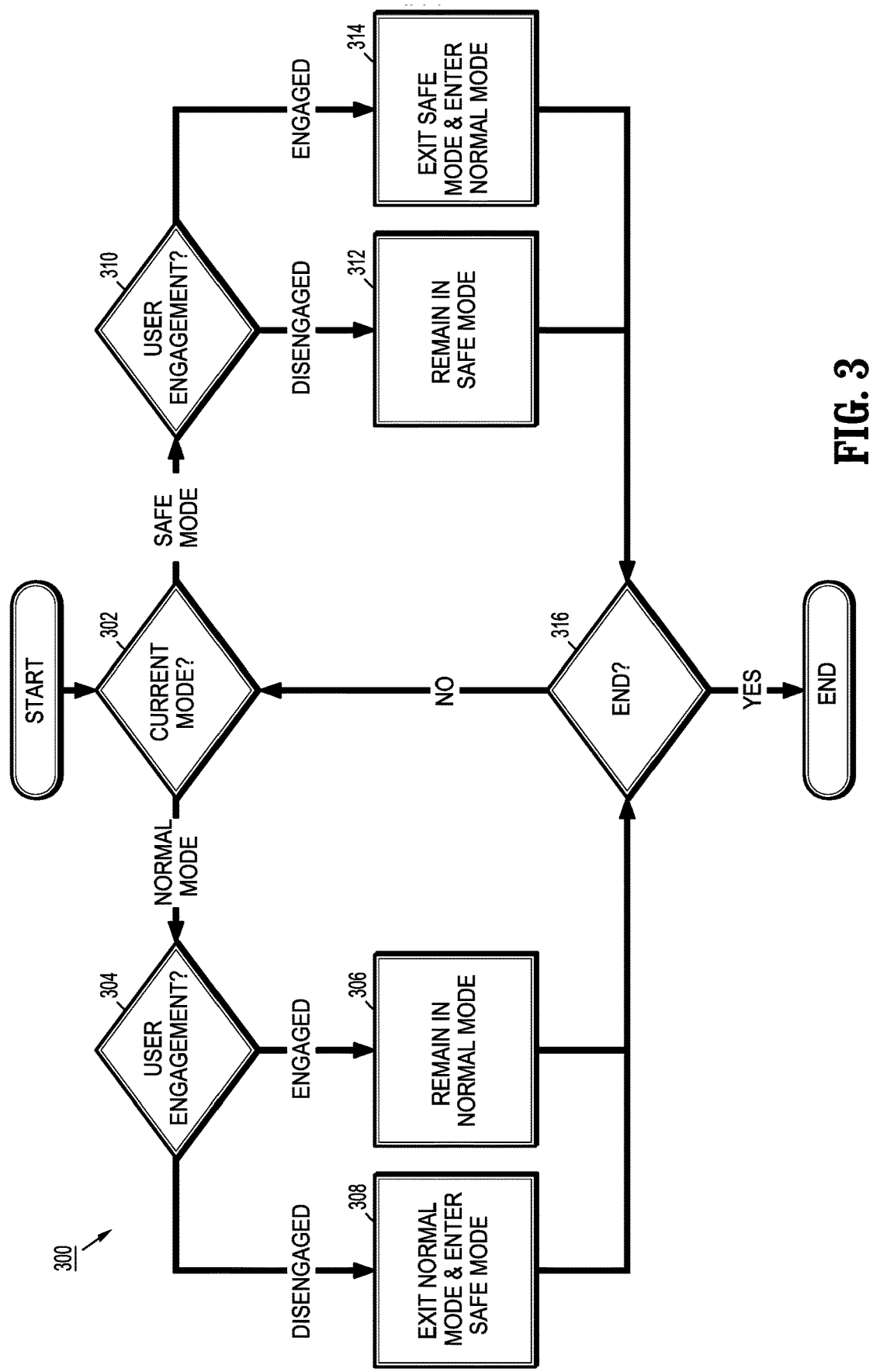
FIG. 3 is a flowchart that illustrates an exemplary method for controlling an operational mode of the robotic surgical system of FIG. 1 based on whether a user is engaged with, or disengaged from, the surgeon console thereof.

FIG. 3 illustrates a method for controlling an operational mode of the robotic surgical system 100 based on whether a user is engaged with, or disengaged from, the, in accordance with an exemplary embodiment herein. At step 302, the surgeon console 170 determines a mode in which the surgeon console 170 is currently operating, such as a safe mode or a normal mode (any mode other than a safe mode). If the surgeon console 170 determines that the surgeon console 170 is currently operating in a normal mode ("NORMAL MODE" at step 302) then processing proceeds to block 304. At block 304, the surgeon console 170 determines whether the user is engaged with, or disengaged from, the surgeon console 170. Exemplary aspects of how the surgeon console 170 makes the determination at step 304 are provided below in connection with FIG. 4 and FIG. 5. In general, the surgeon console 170 may determine whether the user is engaged with, or disengaged from, the surgeon console 170 by tracking a user's head or eye position (for instance, relative to the display device 122), hand position (for instance, contact with handle(s) 112), or any combination thereof. If the surgeon console 170 determines that the user is engaged with the ("ENGAGED" AT BLOCK 304), then processing proceeds to block 306, at which the continues to operate in normal mode. If the surgeon console 170 determines that the user is disengaged with the ("DISENGAGED" AT BLOCK 304), then processing proceeds to block 308, at which the ceases to operate in the normal mode and begins to operate in a safe mode (such as the safe modes described below). From each of steps 306 and 308, processing proceeds to step 316, which is described below.

Referring back to step 302, if the surgeon console 170 determines that the surgeon console 170 is currently operating in a safe mode ("SAFE MODE" at step 302) then processing proceeds to block 310. At block 310, the surgeon console 170 determines whether the user is engaged with, or disengaged from, the surgeon console 170. Exemplary aspects of how the surgeon console 170 makes the determination at step 304 are provided below in connection with FIG. 4 and FIG. 5. If the surgeon console 170 determines that the user is disengaged with the ("DISENGAGED" AT BLOCK 310), then processing proceeds to block 312, at which the continues to operate in the safe mode. If the surgeon console 170 determines that the user is engaged with the ("ENGAGED" AT BLOCK 310), then processing proceeds to block 314, at which the ceases to operate in the safe mode and begins to operate in the normal mode. From each of steps 312 and 314, processing proceeds to step 316.

At step 316, the surgeon console 170 determines whether to terminate the operation of the surgeon console 170, for example, by determining whether a user has inputted a command to shut down the. If the surgeon console 170 determines that operation of the surgeon console 170 is to be terminated ("YES" at 316), then the surgeon console 170 enters an inactive state (for example, a powered down state or a sleep state) and the method 300 is terminated. If the surgeon console 170 determines that operation of the surgeon console 170 is not to be terminated ("NO" at 316), then processing proceeds back to step 302 as described above.

Figure 4:
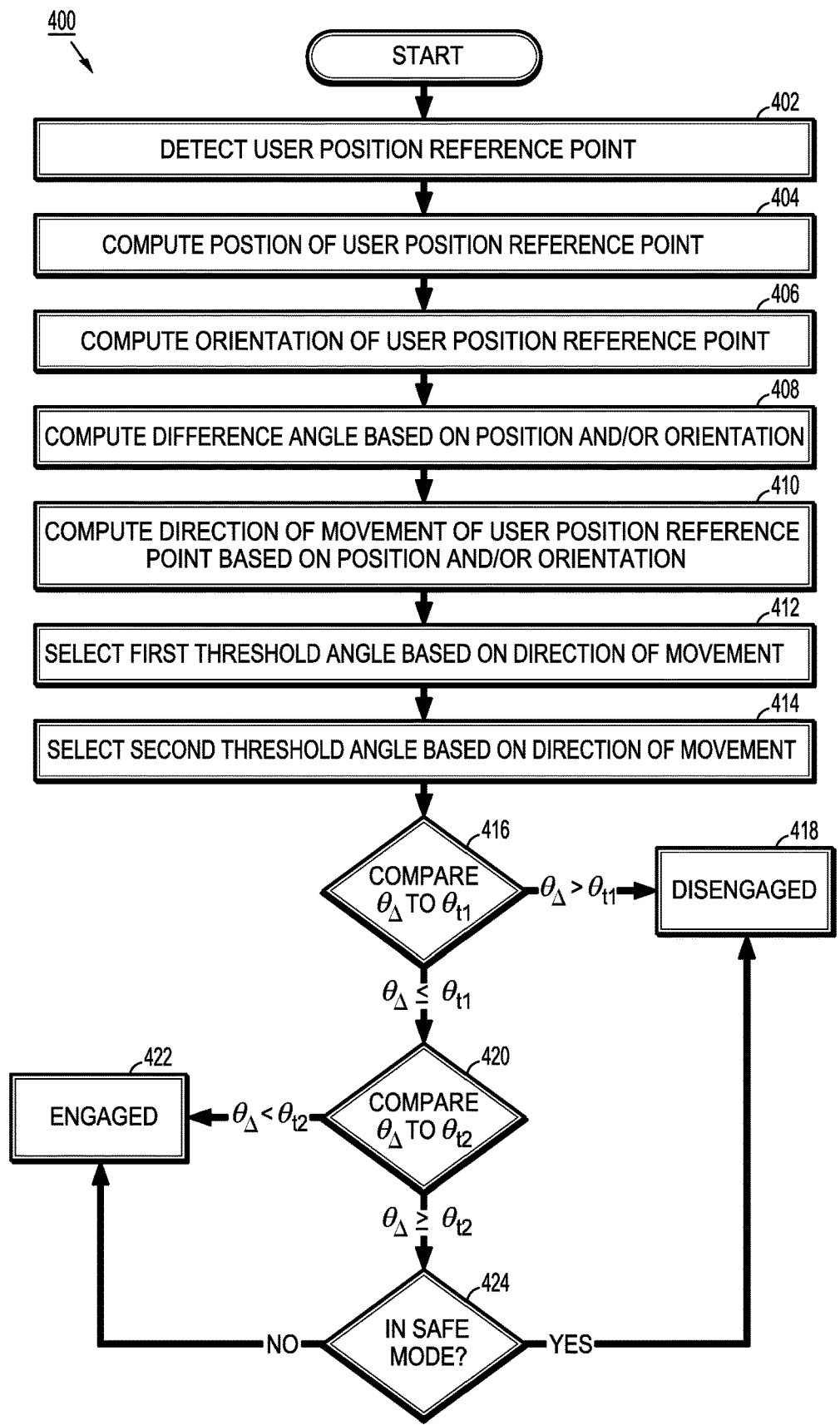
FIG. 4 is a flowchart that illustrates an exemplary method for determining whether a user is engaged with, or disengaged from, a surgeon console of the robotic surgical system of FIG. 1.

FIG. 4 is a flowchart that illustrates an exemplary method for determining whether a user is engaged with, or disengaged from, the surgeon console 170 of the robotic surgical system 100 of FIG. 1. At step 402, the surgeon console 170 detects a user position reference point in one of a variety of ways. For example, in an embodiment where the user position reference point is a portion of the user (such as a head, an eye, and/or the like), the surgeon console 170 may detect the user position reference point by capturing via the image capture device 161 an image including the portion of the user and by executing one or more known image recognition algorithms on the captured image. In an embodiment where the user position reference point is a portion of eyewear 163 worn by the user (such as one or more user position reference points corresponding to three of the markers 164), the surgeon console 170 may detect the user position reference point by capturing via the image capture device 161 an image including the markers 164, and by executing one or more image recognition algorithms on the captured image.

At step 404, the surgeon console 170 computes a position of the detected user position reference point relative to the display device 122. In step 406, the surgeon console 170 computes an orientation of the detected user position reference point relative to the display device 122. In embodiments where the image capture device 161 is equipped with an IR pass filter and IR LEDs and the surgeon console 170 is configured to perform optical tracking, the surgeon console 170 computes the position and orientation of one or more markers relative to the display device 122 and, based on the position and orientation of the one or more markers, computes the position and orientation of the user position reference point and/or of a portion of the user.

In step 408, the surgeon console 170 computes a difference angle $\theta_A$ 201 based on the position and orientation of the user position reference point that were computed at steps 404 and 406, respectively. As described above, in computing the difference angle $\theta_A$ 201, the computes a position of an imaginary line normal to a plane defined by the user position reference point and a position of the imaginary line normal to the front plane of the display device 122, and computes an angle $\theta_A$ 201 between the positions as the difference angle. In step 410, the computes a direction of movement of the user position reference point based on the position and the orientation of the user position reference point that were computed at steps 404 and 406, respectively. In some embodiments, the computes the direction of movement of the user position reference point by comparing the position and orientation of the user position reference point in a current time instance with the position and orientation of a prior time instance.

In step 412, the surgeon console 170 selects a first threshold angle $\theta_{t1}$ (for example, with reference to FIG. 2B and FIG. 2C, $\theta_{t1u}$ 202 for the upward direction or $\theta_{t1d}$ 204 for the downward direction) based on the direction of the movement of the portion of the user. Each possible direction of movement of the user position reference point, or at least a subset of the possible directions of movement of the user position reference point, is associated with a threshold angle, and the association between a threshold angle and the direction of the movement of the user position reference point is specified in a set of rules stored in a memory unit of the surgeon console 170, such as one of the memory units 134, or in a storage device operably coupled to the surgeon console 170. For example, if each cardinal direction of movement, such as up, down, left, right, are associated with a first threshold angle, then the set of rules specify a corresponding first threshold angle $\theta_{t1}$ for each of up, down, left, and right, and the surgeon console 170, using the set of rules, selects a first threshold angle corresponding to the computed direction of movement of the user position reference point.

In some embodiments, a threshold angle associated with one direction of movement is of a different size than a threshold angle associated with another direction of movement. For example, a threshold angle associated with the down direction of movement (for instance, with reference to FIG. 2C, $\theta_{t1d}$ 204) may be larger than the threshold angle associated with the right direction of movement (not shown in FIG. 2C). The size of a threshold angle for a particular direction of movement is based in part on whether a component of the surgical system 100 is positioned in that direction and the distance of that component from the display device 122. For example, if the foot pedal 128 is positioned below the display device 122 then the size of the threshold angle for the down direction should be large enough to accommodate the user looking at the foot pedal 128 without identifying that user as a user that is disengaged from the. In some embodiments, the size of a threshold angle for a particular direction of movement depends upon the likelihood the user of the surgeon console 170 interacts with the component of the surgical system 100 in that direction. For example, if a second display device is positioned to the right of the display device 122, but the second display device does not provide any useful information to the user of the surgeon console 170, then it is unlikely that the user will look at the second display device while still intending to be engaged with the. Thus the threshold angle associated with the direction in which the second display device is positioned, the right direction in this example, should not be large enough to accommodate the user looking at the second display device. However, if the second display device provides useful information to the user or with which the user interacts, then it is more likely that the user will look at the second display device and the size of the threshold angle in that direction should be large enough to accommodate the user looking at the second display device.

In some embodiments, the surgeon console 170 is configured to identify, relative to a user facing the display device 122, the position and orientation of an additional component that is operably and communicatively coupled to the and increase the threshold angle associated with that direction based on the position and the orientation of the additional component. For example, if a display device, additional to the default number of display devices, is operably and communicatively coupled to the surgeon console 170 to the right side of a user facing the surgeon console 170, then the surgeon console 170 increases the threshold angle associated with the right direction of the user based on the position and orientation of the additional display device relative to the user facing the display device 122 or using the surgeon console 170. In some embodiments, the position and orientation of an additional component that is operably and communicatively coupled to the surgeon console 170 is provided to the surgeon console 170 as an input, and the surgeon console 170 determines the direction, relative to the user of the surgeon console 170, in which the additional component is located, computes an increase in the size of the threshold angle associated with that direction, and increases that threshold angle by that computed increase in size.

Thus, by specifying different threshold angles for different direction of movements, the surgeon console 170 reduces the possibility of falsely identifying a user as being disengaged from the surgeon console 170 when the user is engaged with the. Reducing such false identifications, further reduces falsely causing the surgical system 100 to initiate and operate in a safe mode and improves overall efficiency of the surgical system 100.

In some embodiments, each direction of movement is also associated with a second threshold angle $\theta_{t2}$ (for example, with reference to FIG. 2B and FIG. 2C, $\theta_{t2u}$ 203 for the upward direction or $\theta_{t2d}$ 205 for the downward direction), smaller than the first threshold angle $\theta_{t1}$ (for example, $\theta_{t1u}$ 202 for the upward direction or $\theta_{t1d}$ 204 for the downward direction), and the set of rules specifies the associated second threshold angle $\theta_{t2}$ for each direction of movement. In such embodiments, in step 414, the surgeon console 170, using the set of rules, selects a second threshold angle $\theta_{t2}$ corresponding to the direction of movement of the user position reference point computed at step 410. The second threshold angle $\theta_{t2}$ is used to determine whether a user, who has been identified as being disengaged from the surgeon console 170, is re-engaged with the surgeon console 170. By providing a second threshold angle $\theta_{t2}$ smaller than the first threshold angle $\theta_{t1}$, the surgical system 100 creates a buffer that prevents the surgical system 100 from quickly oscillating between operating in a safe mode and non-safe mode.

In step 416, the surgeon console 170 compares the difference angle $\theta_A$ 201, which was computed at step 408 based on the position and the orientation of the user position reference point computed at steps 404 and 406, respectively, is greater than the first threshold angle $\theta_{t1}$. If the surgeon console 170 determines that the difference angle $\theta_A$ 201 is greater than the first threshold angle $\theta_{t1}$ ("$\theta_A > \theta_{t1}$" at step 416), then, in step 418, the surgeon console 170 determines that the user is disengaged. In some embodiments, as described above in connection with steps 308 and/or 312 of FIG. 3, the, in response to identifying the user as being disengaged, causes the surgical system 100 to operate in a selected safe mode, for instance, by initiating and processing steps associated with the selected safe mode.

In some embodiments, the surgeon console 170 is configured with an indicator, stored in a memory unit 134 or in a storage device operably coupled to the surgeon console 170, the value of which indicates whether the surgical system 100 is operating in a safe mode or a non-safe mode, referred to herein as "safe mode indicator," and the surgeon console 170 determines whether the surgical system 100 is operating in a safe mode based at least in part on the value of the safe mode indicator. The is configured to update the value of the safe mode indicator to indicate that the surgical system 100 is operating in a safe mode at a time when the surgical system 100 is caused to operate in a safe mode or at a time when the user is identified as being disengaged from the. Examples of a safe mode indicator include, but are not limited to, a flag variable, the value of which the surgeon console 170 updates to indicate whether the surgical system 100 is operating in a safe mode, for example by setting the value of the flag variable to a one (1) to indicate that the surgical system 100 is operating in a safe mode and to a zero (0) to indicate that the surgical system 100 is operating in a non-safe mode.

In some embodiments, the surgeon console 170 is configured to select a default safe mode specified in a set of rules stored in a memory unit of the surgeon console 170, such as memory units 134 or storage device operably coupled to the. In some embodiments, a list of multiple safe modes, each of which is associated with a ranking, is stored in one or more memory units 134 or a storage device operably coupled to the surgeon console 170, and the is configured to select from the list of multiple safe modes based on the ranking associated with the safe modes. In some embodiments, the provides a GUI presenting a list of various safe modes in which the surgical system 100 is configured to operate and the user selects a safe mode and provides the selection as an input to the surgeon console 170 using the GUI. Additional details of some of the safe modes in which the surgical system 100 is configured to operate are provided herein in the contexts of FIG. 6 and FIG. 7.

In step 416, if the surgeon console 170 determines that the difference angle $\theta_A$ 201 is not greater than the first threshold angle $\theta_{t1}$ ("$\theta_A<\theta_{t1}$" at step 416), then, in embodiments where a second threshold angle $\theta_{t2}$ is associated with a direction of movement and the second threshold angle $\theta_{t2}$ is selected, the proceeds to step 420. In step 420, the surgeon console 170 compares the difference angle $\theta_A$ to the second threshold angle $\theta_{t2}$. If the surgeon console determines that the difference angle $\theta_A$ is less than the second threshold angle $\theta_{t2}$ ("$\theta_A<\theta_{t2}$" at step 420), then, in step 422, the surgeon console 170 determines that the user is engaged. In embodiments, the surgeon console 170 may further determine an XYZ position of the user (that is, determine a position of the user's head, face, or 3D glasses in three-dimensional space relative to the surgeon console 170) to determine whether the user is engaged. For example, by determining the XYZ position of the user relative to the, the can determine whether the user is too far away from the surgeon console and provide a notification indicating such. Additionally, in embodiments where multiple individuals are within a predetermined distance of the, the can ensure that the correct individual (i.e. the user) is tracked and that another individual standing behind the user is not determined as engaged with the surgeon console 170.

If the surgeon console 170 determines that the difference angle $\theta_A$ is not less than the second threshold angle $\theta_{t2}$ ("$\theta_{66}>\theta_{t2}$" at step 420), then, at step 424, the surgeon console 170 determines whether the surgical system 100 is operating in a safe mode. In some embodiments, the surgeon console 170 may additionally determine whether a displacement of the user is larger than a predetermined threshold. Additionally or alternatively, the surgeon console 170 may determine a displacement gradient. By determining the displacement gradient and/or whether the displacement is larger than a predetermined threshold, the surgeon console 170 may determine if a displacement is too large over too short a period of time, as may be the case if there are multiple individuals in an engagement zone of the surgeon console 170 and movement of an individual other than the user is mistakenly attributed to the user or the tracker jumps from one user to another. If it is determined that the displacement is larger than the predetermined threshold or the displacement gradient indicates that the tracker may have jumped between individuals, the safe mode may be activated. If the surgeon console 170 determines that the surgical system 100 is operating in a safe mode ("YES" at step 424), then, in step 418, the surgeon console 170 identifies the user as disengaged with the. If the surgeon console 170 determines that the surgical system 100 is not operating in a safe mode ("NO" at step 424), then, in step 422, the surgeon console 170 identifies the user as being engaged (or re-engaged, as the case may be) with the surgeon console 170. As described above in connection with steps 306 and/or 314 of FIG. 3, the surgeon console 170, in response to identifying the user as being engaged, causes the surgical system 100 to operate in a normal (non-safe) mode, for instance, by initiating and processing steps associated with the normal mode. In some embodiments, in step 420, the surgeon console 170 is configured to wait for a threshold amount of time prior to identifying the user as being re-engaged with the surgeon console 170. In embodiments where the surgeon console 170 is configured with a safe mode indicator, the surgeon console 170 updates the value of the safe mode indicator to indicate that the surgical system 100 is not operating in a safe mode at time when the user is identified as re-engaged or engaged with the surgeon console 170 or at a time when the surgical system 100 is caused to exit the safe mode.

Figure 5:
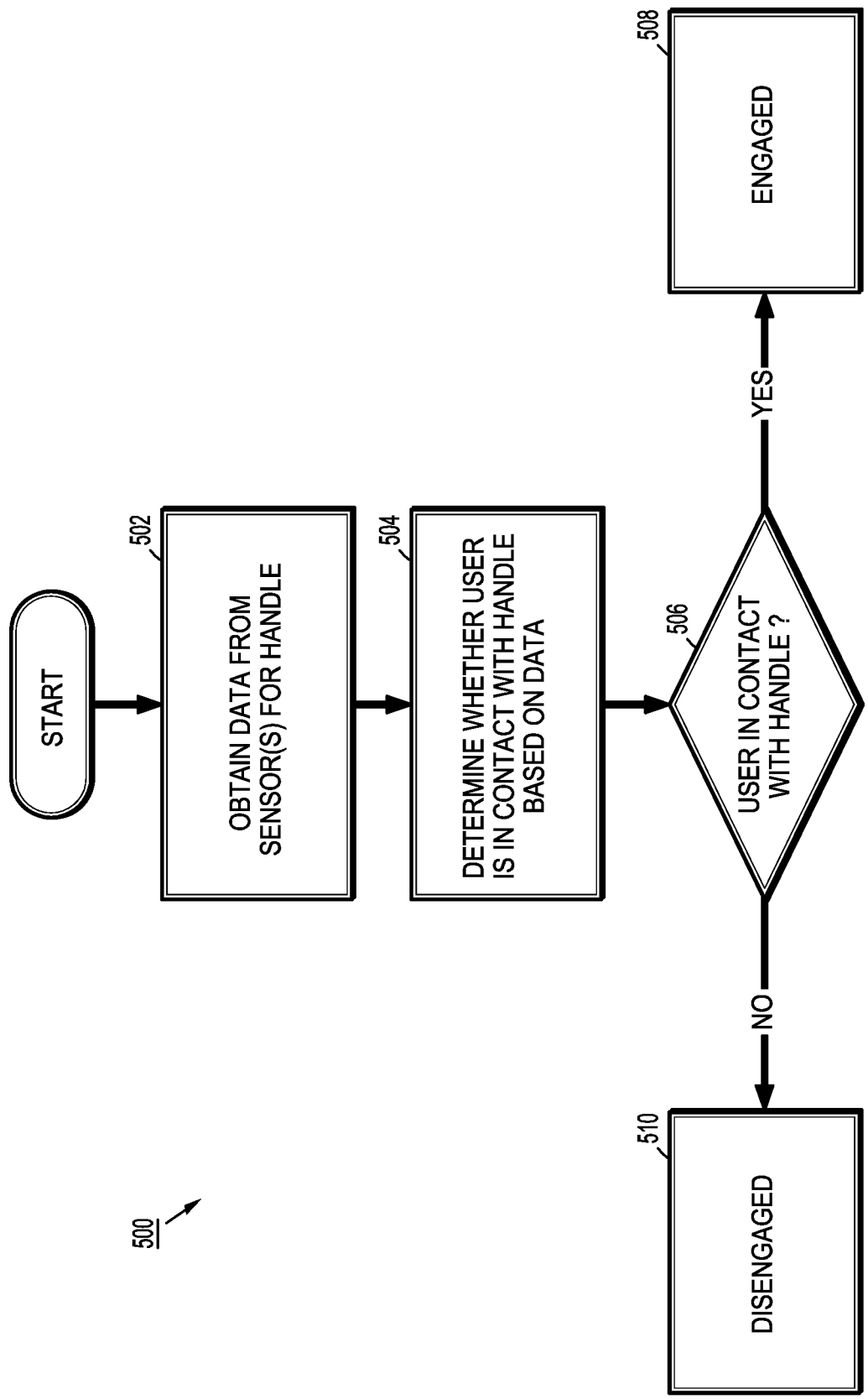
FIG. 5 is a flowchart that illustrates another exemplary method for determining whether a user is engaged with, or disengaged from, a surgeon console of the robotic surgical system of FIG. 1.
Figure 6:
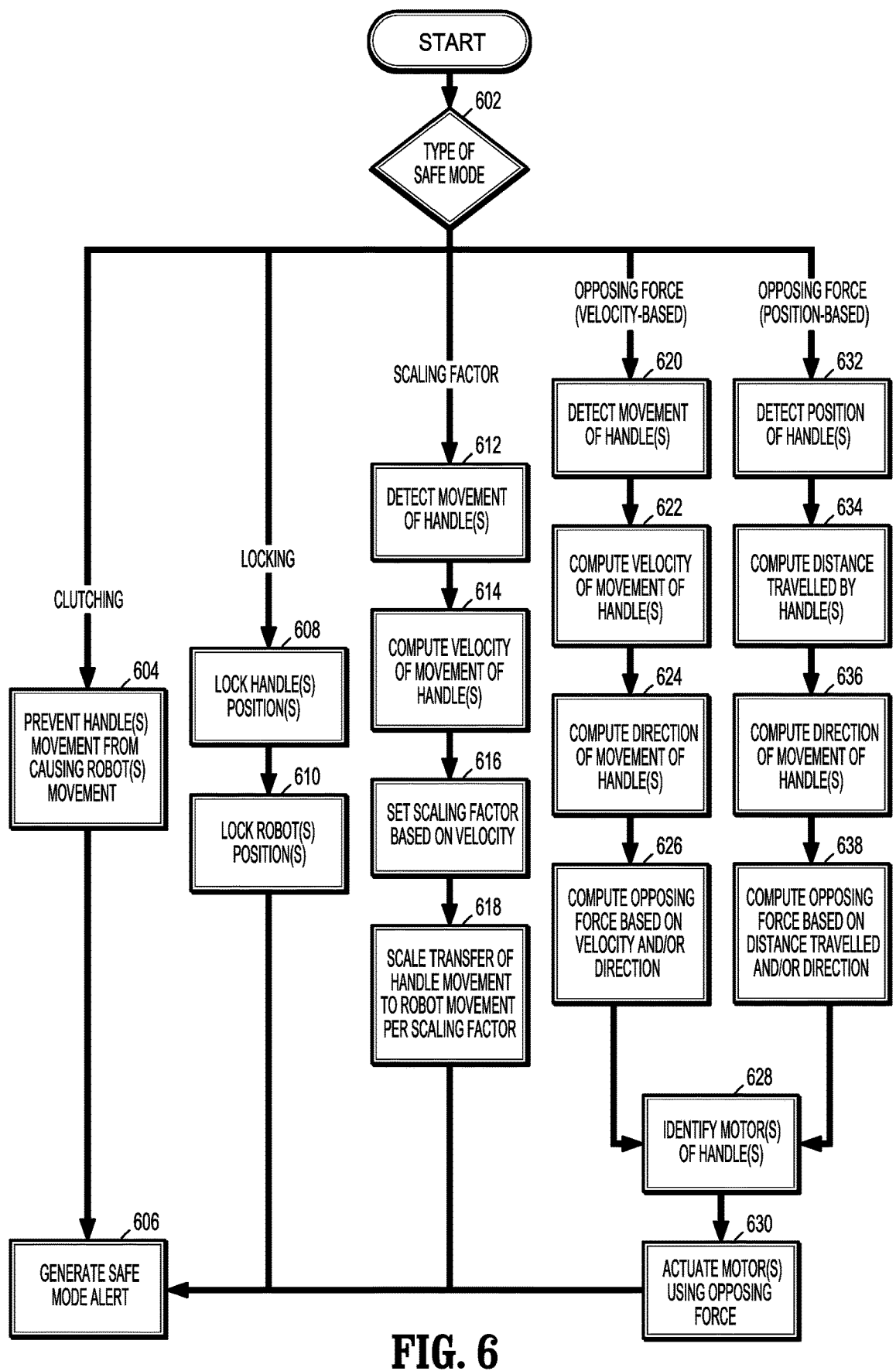
FIG. 6 is a flowchart that illustrates an exemplary method for operating the robotic surgical system of FIG. 1 in one or more safe modes of operation.

FIG. 5 shows another illustrative method 500 of determining whether the user of the surgeon console 170 is engaged or disengaged from the surgeon console 170. In various embodiments, the surgeon console 170 may be configured to determine whether the user is engaged with, or disengaged from, the surgeon console 170 by employing the method 300 (FIG. 3) and/or the method 400 (FIG. 4) either individually or in any combination with one another.

At step 502, processor 133 of the surgeon console 170 obtains data from one or more sensor(s) 130 indicating whether the user is in contact with one or more handles 112 of the surgeon console 170. At step 504, the surgeon console 170 determines whether the user is in contact with the handles 112 based on the data obtained at step 502. In particular, for instance, the may determine at step 504 whether the user is in contact with a handle 112A based on outputs from one or more sensors 130A, such as capacitive and/or optical sensors, that are coupled to the handle 112A and configured to identify the user's contact with the handle 112A. Exemplary types of outputs from such sensor 130A include, but are not limited to, a high signal or a one (1) when a user is in contact with a handle 112A coupled to the sensors and a low signal or a zero (0) when the user is not in contact with the handle 112A. For example, the sensor 130A is a capacitive sensor configured to transmit a high signal or a one (1) to the processor 133 of the when the user is in contact with the handle 112A and a low signal or a zero (0) when the user is not in contact with the handle 112A, then the surgeon console 170 determines that the user is in contact with the handle 112A if a high signal or a 1 is received by the processor 133 from the capacitive sensor 130A and that the user is not in contact with the handle 112A if a low signal or a zero (0) surgeon console 170 is received by the processor 133 from the capacitive sensor 130A. In some embodiments, the surgeon console 170 determines that the user is in contact with the surgeon console 170 if the user is simultaneously in contact with a majority of the handles 112. For example, if the surgeon console 170 includes three handles 112 and the surgeon console is configured to determine that a user is in contact with the surgeon console 170 if the user is contact with a majority of the handles 112, then the surgeon console 170 determines that the user is in contact with the surgeon console 170 if the user is simultaneously in contact with at least two of the handles 112. Similarly, if the surgeon console 170 includes two handles 112, then the surgeon console 170 determines that the user is in contact with the surgeon console 170 if the user is in contact with both of the handles 112, a majority of the handles 112 of the.

In step 506, if the surgeon console 170 determines that the user is not in contact with the surgeon console 170 ("NO" at step 506), then, in step 510, the surgeon console 170 identifies the user as disengaged from the surgeon console 170. In step 506, if the surgeon console 170 determines that the user is in contact with the surgeon console 170 ("YES" at step 506), then, in step 508, the surgeon console 170 identifies the user as re-engaged with the surgeon console 170.

As described above, the surgical system 100 is configured to operate in one or more safe modes, either individually or in any combination, and additional details of these safe modes are provided herein in the contexts of FIG. 6 and FIG.

Figure 7:
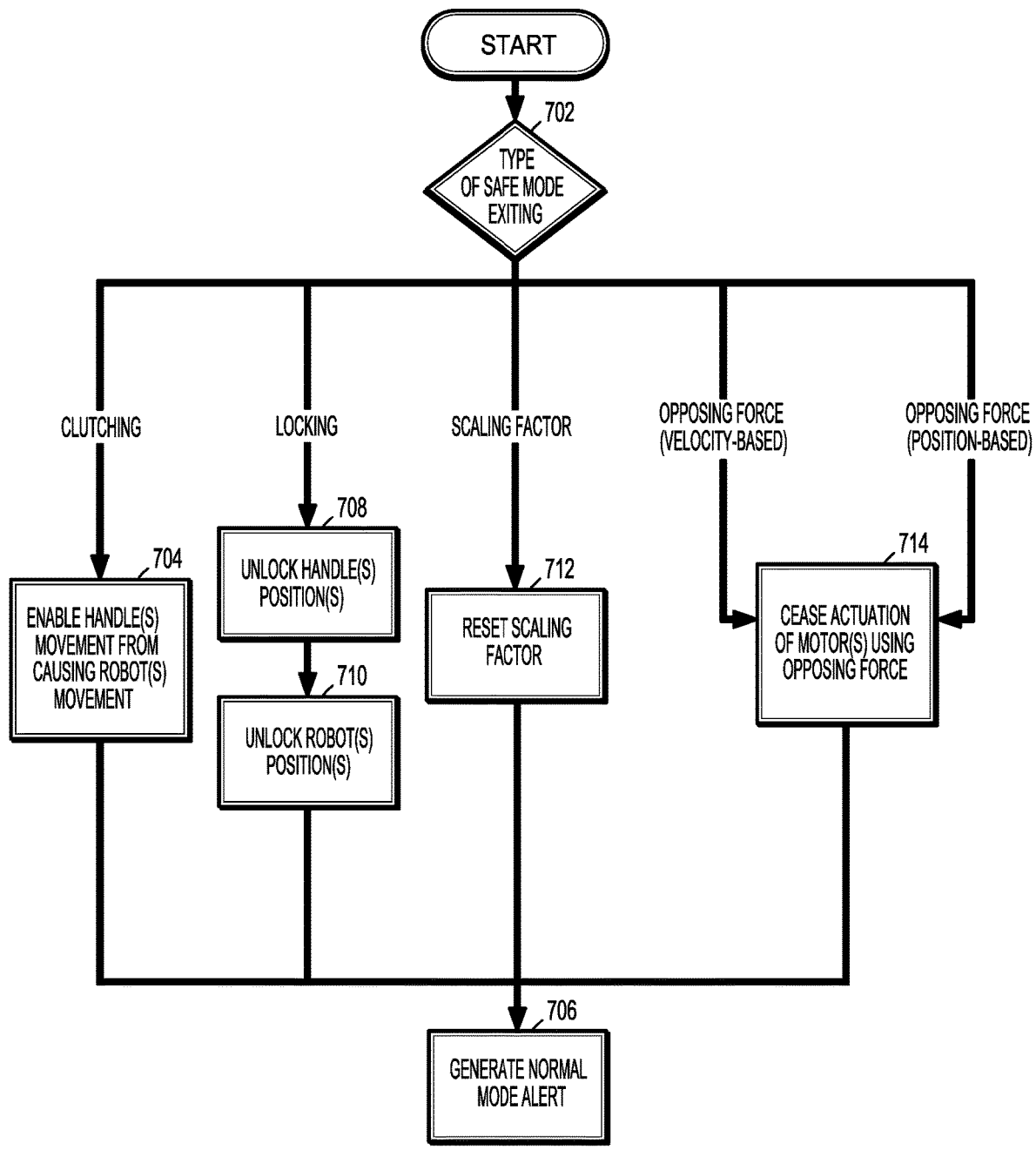
FIG. 7 is a flowchart that illustrates an exemplary method for terminating one or more safe modes of operation of the robotic surgical system of FIG. 1.
Figure 8:
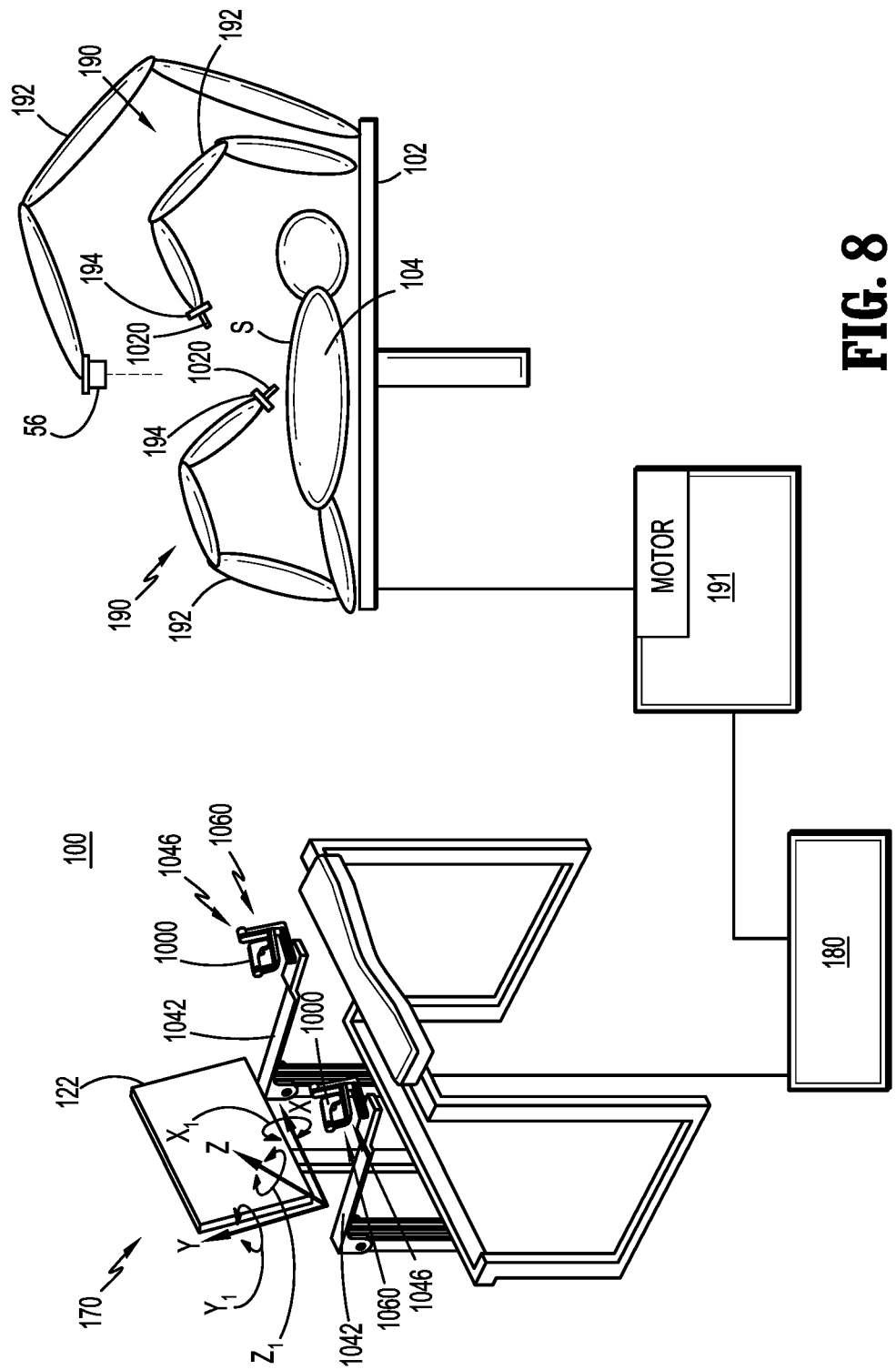
FIG. 8 is a schematic illustration of the robotic surgical system including a robot system and a user interface or surgeon console, in accordance with an embodiment of the present disclosure.

7. In particular, FIG. 6 and FIG. 7 shows a flowchart that illustrates an exemplary method 600 for operating the robotic surgical system 100 of FIG. 1 in one or more of the following five illustrative safe modes of operation: (1) a clutching safe mode, (2) a locking safe mode, (3) a scaling factor safe mode, (4) an opposing force safe mode based on handle velocity, and (5) an opposing force safe mode based on handle position. In some embodiments, the surgical system 100 is configured to enter (see, for example, step 308 of FIG. 3) or remain in (see, for example, step 312 of FIG. 3) one or more of the safe modes according to the method 600, based on a determination (see, for example, steps 304 and/or 310 of FIG. 3, method 400 of FIG. 4, and/or method 500 of FIG. 5) as to whether the user is engaged with, or disengaged from, the surgeon console 170. Referring now to FIG. 6, at step 602, the surgeon console 170 determines which safe mode to enter or remain in, for instance, based on a value of the safe mode indicator described above. Although some safe modes are described herein in the context of controlling one of the robot assemblies 190 or subunits 191, 192, 193, and 194 thereof, in various embodiments, safe modes include simultaneously controlling multiple robot assemblies 190 and/or the subunits 191, 192, 193, and 194 thereof.

If the surgeon console 170 determines to enter or remain in the clutching safe mode ("CLUTCHING" at step 602), then processing proceeds to step 604. While the surgical system 100 is operating in a non-safe mode, the surgeon console 170 causes one or more of the subunits 191, 192, 193, and 194 of the robot of assemblies 190 to be moved by transmitting data related to the movement of the handles 112 of the to one or more of the subunits 191, 192, 193, and 194 of the robot assemblies 190 that are communicatively coupled to the handles 112, and one or more of the subunits 191, 192, 193, 194 that receives data related to the movement of the handles 112 moves based in part on the received data.

In step 604, while the surgical system 100 operates in the clutching safe mode, for each handle 112 of the surgeon console 170, the surgeon console 170 prevents movement of the handle 112 from causing a corresponding movement of the one or more of the subunits 191, 192, 193, and 194 of the robot assembly 190 communicatively coupled to that handle 112, for instance, by preventing the transmission of data related to the movement of the handle 112 to the subunit(s) 191, 192, 193, and/or 194. In some embodiments, the surgeon console 170 is configured with an indicator, stored in a memory unit 134 or in a storage device operably coupled to the surgeon console 170, the value of which indicates whether the clutching safe mode is enabled or disabled, referred to herein as "clutching safe mode indicator," and the surgeon console 170 determines whether to transmit data related to the movement of the handles 112 based in part on the values of the movement translation indicator. Examples of values of the clutching safe mode indicator that indicate that clutching safe mode is disenabled is a one (1) or a sequence of ones (e.g. "11111"), and the examples of values of the clutching safe mode indicator that indicate that the clutching safe mode is enabled is a zero (0) or a sequence of zeroes (e.g. "00000"). In some embodiments, each bit of the value of the clutching safe mode indicator is associated with a handle 112 of the surgeon console 170, and the surgeon console 170 determines whether to transmit movement data of a particular handle 112 based in part on the value of the bit associated with that handle 112. For example, the zero$^{th}$ bit of the value may be associated with the handle 112A and the first bit of the value may be associated with the handle 112B, and the surgeon console 170 determines whether to transmit data related to the movement of the handle 112A based on whether the zero$^{th}$ bit is high (1) or low (0), and the surgeon console 170 determines whether to transmit data related to the movement of the handle 112B based on whether the first bit is high or low.

The surgeon console 170 is configured to update the value of the clutching safe mode indicator to indicate that the clutching safe mode is enabled at a time when translation of movement from the movement of the handle 112 to the movement of the communicatively coupled robot arm is disabled. From step 604, processing proceeds to step 606, at which the surgeon console 170 provides an alert to the user that indicates that the surgeon console 170 is in a safe mode (in this case, the clutching safe mode. Examples of the alerts that may be provided at step 606 include, but are not limited to, visual and/or auditory alerts, similar to the alerts described above.

Referring back to step 602, if the surgeon console 170 determines to enter or remain in the locking safe mode ("LOCKING" at step 602), then processing proceeds to step 608. At step 608, the surgeon console 170 locks each handle 112 of the surgeon console 170 in its position and prevents the movement of the handles 112 from their positions. In some embodiments, the surgeon console 170 identifies the position of each of the handles 112 at the time of locking the handles 112 and stores data related to the positions of the handles 112 in a memory unit 134 of the surgeon console 170 or a storage device operably coupled to the surgeon console 170. In some embodiments, the surgeon console 170 locks the handles 112 in their position by preventing movement of the motors and actuators of the handles 112, such as motors 132A and 132B. For example, the surgeon console 170 may cause the motors to servo or apply torque to restore the handles 112 to the stored position such that each subunit 191, 192, 193, 194 that is locked maintains the stored position. In step 610, the surgeon console 170 causes each of the subunits 191, 192, 193, 194 that are communicatively coupled to the handles 112 to be locked in its position by transmitting a lock instruction to each of the subunits 191, 192, 193, 194. As described above, the surgeon console 170 is communicatively coupled to the robot assemblies 190, via the computing device 180 and the surgeon console 170 transmits instructions to lock the subunits 191, 192, 193, 194 to the robot assemblies 190 by transmitting the instructions to the computing device 180, which in turn transmits the instructions to the robot assemblies 190. In some embodiments, the surgeon console 170 is directly communicatively coupled to each robot assembly 190 of the surgical system 100 and the surgeon console 170 transmits instructions to lock the robot arms in their positions directly to the robot assemblies 190 of the robot arms communicatively coupled to the handles 112. Each robot assembly that receives the instructions, locks its robot arm in its position in response to receiving the instructions.

From step 610, processing proceeds to step 606, at which the surgeon console 170 provides an alert to the user that indicates that a safe mode (the locking safe mode, in this instance) is activated. In some embodiments, the surgeon console 170 provides a visual alert indicating that the handles 112 and the communicatively coupled robot arms are locked. An example of the visual alert includes, but is not limited to, a graphical item displayed on one or more display devices of the surgeon console 170, such as the display device 122. Another example of the visual alert includes a light emitting diode (LED) on the surgeon console 170 that is powered on at the time the handles 112 and the communicatively coupled robot arms are locked. In some embodiments, the surgeon console 170 is configured to provide an auditory alert, such as a sound recording, and/or a tactile alert such as vibration or other physical feedback that indicates that the handles 112 and the communicatively coupled robot arms are locked.

Referring back to step 602, if the surgeon console 170 determines to enter or remain in a scaling factor safe mode ("SCALING FACTOR" at step 602), then processing proceeds to step 612. At step 612, the surgeon console 170 detects movement of the handle 112 of the surgeon console 170. As described above, each handle 112 is operably and communicatively coupled to one or more sensors 130 that are configured to detect movement of the handle 112 and the velocity of the movement of the handle 112 and output values that indicate whether the handle 112 is moved and/or the velocity of the handle 112. Based on the output values of the one or more sensors 130 coupled to the handle 112, the surgeon console 170 detects movement of the handle 112. At step 614, the surgeon console 170 computes a velocity at which the handle 112 is moved. As described above, the surgeon console 170 computes the velocity based on based on multiple positions of the handle sensed over time via the one or more sensors 130 coupled to the handle 112 and configured to sense movement of the handle 112.

At step 616, the surgeon console 170, based on the velocity of the movement of the handle 112 computed at step 614, selects a scaling factor from a list of safe-mode scaling factors. As used herein, the term "scaling factor" refers to a ratio between a movement of a handle 112 to a corresponding movement that is caused of one or more subunits 191, 192, 193, and 194 communicatively coupled to the handle 112. For example, a scaling factor of 3:1 indicates that a movement of the handle 112 by three inches translates to a movement of the communicatively coupled subunit 191, 192, 193, and/or 194 by 1 inch. Similarly, a scaling factor of 50:1 indicates that movement of the handle 112 by 5 inches translates to a movement of the communicatively coupled subunit 191, 192, 193, and/or 194 by 0.1 inch. A safe mode scaling factor is a scaling factor specified in a set of rules or configuration data, which the surgeon console 170 is configured to use if the surgical system 100 is operating in a scaling factor safe mode. The set of rules or configuration data further specify a velocity or a range of velocities for each safe mode scaling factor, and are stored in one or more memory units of the memory units 134 or a storage device operably coupled to the surgeon console 170. In some embodiments, in selecting a scaling factor from the list of safe mode scaling factors, the surgeon console 170 identifies the velocity that is closest to the computed velocity of the handle 112 or the range of velocities which includes the computed velocity, and selects the associated scaling factor. In other embodiments, the surgeon console 170 computes a velocity of a movement of the handle 112 and modifies the downward scaling factor based on the computed velocity.

At step 618, the surgeon console 170 applies the safe mode scaling factor selected at step 616 to the distance travelled by the handle 112 to compute the scaled distance, and transmits the scaled distance to one or more of the subunits 191, 192, 193, or 194 communicatively coupled to the handle 112, which move based in part on the received scaled distance. The selected safe mode scaling factor may, in some examples, be a downward scaling factor that, relative to a non-safe mode scaling factor, causes a small amount of movement of one or more of the subunits 191, 192, 193, or 194 for a given amount of movement of the handle 112. In some embodiments, the surgeon console 170 transmits the selected safe-mode scaling factor and the distance travelled by the handle 112 to a particular one or more of the subunits, 191, 192, 193, and/or 194, and the scaled distance is computed based in part upon which the robot arm is moved. After step 710, the surgeon console 170 returns to step 302 (shown in FIG. 3A). From step 618, processing proceeds to step 606, at which the surgeon console 170 provides a visual and/or an auditory alert to the user indicating that the safe mode based on handle velocity is enabled.

Referring again to step 602, if the surgeon console 170 determines to enter or remain in the opposing force safe mode based on handle velocity ("OPPOSING FORCE (VELOCITY-BASED)" at step 602), then processing proceeds to step 620. At step 620, the surgeon detects movement of one or more of the handles 112. The surgeon console 170 detects movement of the handles 112 in a similar manner as described above for step 612. At step 622, the surgeon console 170 computes the velocity of the movement of the handle 112 using the one or more sensors 130 that are operably and communicatively coupled to the handle 112.

At step 624, the surgeon console 170 computes a direction of the movement of the handle 112. As described above, one or more of the sensors 130 are configured to sense a direction of movement of the handle 112 in one or more directions, and the surgeon console 170 computes the direction of the movement of the handle 112, for example relative to a prior position of the handle 112, based on the outputs from the one or more sensors 130.

In step 626, the surgeon console 170, based on the computed velocity of the movement of the handle 112 and the computed direction of the movement of the handle 112, computes an opposing force to be applied to the handle 112 in a direction opposite to the computed direction of movement of the handle 112. At step 628, the surgeon console 170 identifies a motor, among the motors 132 of the handle 112, associated with the direction in which the opposing force computed at 626 is to be applied, and, at step 630, the surgeon console 170 actuates the identified motor in the direction opposite to the computed direction of movement of the handle 112 at a speed sufficient to generate the opposing force computed at step 626 in the direction opposite to the computed direction of handle movement and thereby significantly reduce any travel of the handle 112. Thus, the surgeon console 170 provides sufficient force to the user in the direction opposite to the direction of movement of handle 112, thereby providing a haptic feedback to the user that the surgical system 100 is operating in a safe mode. From step 630, processing proceeds to step 606 to provide an alert that the safe mode (the opposing force safe mode based on velocity, in this instance) is activated.

Referring again to step 602, if the surgeon console 170 determines to enter or remain in the opposing force safe mode based on handle position ("OPPOSING FORCE (POSITION-BASED)" at step 602), then processing proceeds to step 632. At step 632, for each handle 112, the surgeon console 170 identifies the position of the handle 112 at the time the surgical system 100 is caused to operate in the opposing force safe mode based on handle position. The surgeon console 170 stores the identified position of the handle 112 in a memory unit 134 or a data storage device operably coupled to the surgeon console 170.

At step 634, the surgeon console 170 detects movement of one or more of the handles 112 from its respective position identified at step 632. At step 634, the surgeon console 170 computes a distance traveled by the handle(s) 112 that moved. As described above, one or more sensors 130 coupled to the handles 112 is configured to sense a distance the handle 112 travels and the surgeon console 170 computes the distance traveled by the handles 112 using the data from the one or more sensors 130.

At step 636, the surgeon console 170 computes a direction of the movement of the handle 112 and, at step 638, based on the computed velocity of the movement of the handle 112 and/or the computed direction of the movement of the handle 112, the surgeon console 170 computes an opposing force to be applied to the handle 112 in a direction opposite to the computed direction of handle movement. At step 628, the surgeon console 170 identifies a motor, among the motors 132 of the handle 112, associated with the computed direction of movement, and, at step 630, the rotates the identified motor at a speed sufficient to generate the computed opposing force in the direction opposite to the computed handle movement direction, and continues to actuate the motor until the handle 112 returns to the position identified at step 632, thereby reducing any travel of the handle 112 and providing feedback to the user indicating that the motion is being resisted, thereby alerting the user that the surgical system 100 is operating in a safe mode.

FIG. 7 is a flowchart that illustrates an exemplary method 700 for terminating one or more safe modes of operation of the robotic surgical system 100 of FIG. 1. At step 702, the surgeon console 170 determines which safe mode to exit, for instance, based on a value of the safe mode indicator described above. If the surgeon console 170 determines to exit the clutching safe mode ("CLUTCHING" at step 702) then processing proceeds to step 704. At step 704, for each handle 112 of the surgeon console 170, the surgeon console 170 enables the translation of movement from the movement of the handle 112 to the movement of the subunit 191, 192, 193, and/or 194 communicatively coupled to the handle 112 by enabling the transmission of data related to the movement of the handle 112 to the subunit(s) 191, 192, 193, or 194. In embodiments where the surgeon console 170 is configured with a clutching safe mode indicator, the surgeon console 170 updates the value of the clutching safe mode indicator to a value that indicates that the clutching safe mode is disabled. At step 706, the surgeon console 170 provides an alert to the user that indicates that the clutching safe mode is disabled and/or that the normal (non-safe) mode is enabled.

If the surgeon console 170 determines to exit the locking safe mode ("LOCKING" at step 702) then processing proceeds to step 708. At step 708, the surgeon console 170 unlocks each handle 112 of the surgeon console 170. In some embodiments, the surgeon console 170 unlocks each handle 112 by actuating the motors 132 associated with the handle 112 as per their non-safe mode configuration in response to the user moving the handle 112. For example, the surgeon console 170 may unlock each handle 112 when it is determined that the surgeon is re-engaged (e.g. looking at the surgeon console 170), and/or surgeon console 170 after the user performs a predetermined action, such as actuating a button or pedal or performing a particular motion of the handle 112. At step 710, the causes each subunit 191, 192, 193, or 194 communicatively coupled to the handles 112 to be unlocked by, for example, transmitting to the computing device 180 instructions to unlock the subunit(s) 191, 192, 193, or 194, in response to which, the computing device 180 transmits the instructions to the subunit(s) 191, 192, 193, or 194. In embodiments where the robot assemblies 190 are directly connected to the surgeon console 170, the surgeon console 170 transmits the instructions to release the robot arms directly to the robot assemblies 190 of the robot arms communicatively coupled to the handles 112. Each robot assembly that receives the instructions, unlocks its subunit 191, 192, 193, and/or 194 in response to receiving the instructions.

At step 706, the surgeon console 170 provides an alert to the user that indicates that the safe mode has been exited and/or that the normal mode (non-safe mode) has been entered. In one example, the alert includes indicating that the handles 112 and the robot arms communicatively coupled to the handles 112 are unlocked. The alerts provided to the user, in some embodiments, are visual alerts and, in some embodiments, are auditory alerts. Examples of the visual alerts include, but are not limited to, graphical items displayed on one or more display devices of the and LEDs on the.

Referring back to step 702, if the determines to exit the scaling factor safe mode ("SCALING FACTOR" at step 702) then processing proceeds to step 712. At step 712, the surgeon console 170 resets the scaling factor back to a predetermined value, such as a 1:1 value, to be used during normal (non-safe mode) operation.

If the determines to exit either the opposing force safe mode based on handle velocity or the opposing force safe mode based on handle position ("OPPOSING FORCE (VELOCITY BASED)" or "OPPOSING FORCE (POSITION-BASED)" at step 702) then processing proceeds to step 714. At step 714, the surgeon console 170 ceases actuation of the motors initiated at step 630 of FIG. 6. From step 714, processing proceeds to step 706, at which an alert is generated indicating that the safe mode has been disabled and the normal mode has been enabled.

Figure 9:
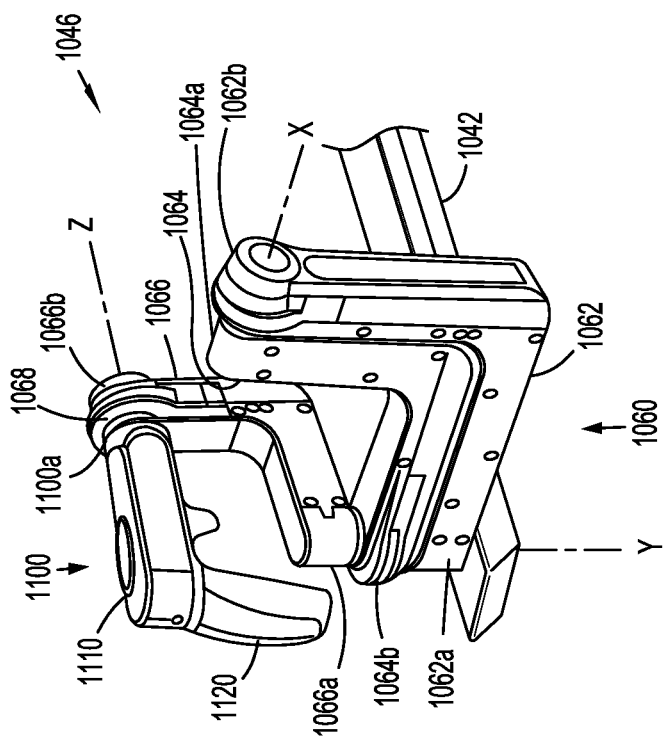
FIG. 9 is an enlarged perspective view of control arm assemblies of the user interface of FIG. 8.
Figure 9:
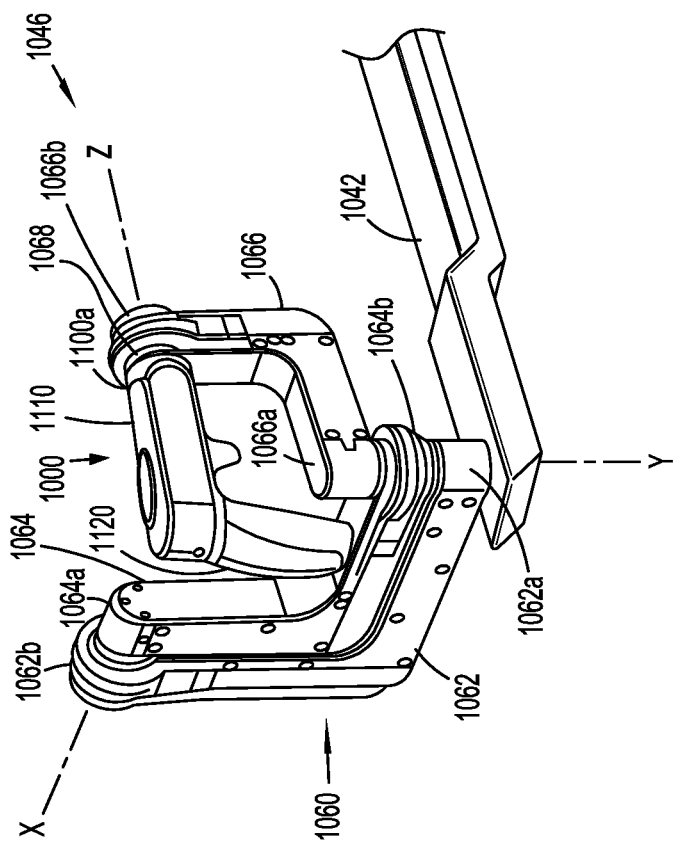

Turning now to FIG. 9, a robotic surgical system 100 in accordance with the present disclosure is once again shown. The robotic surgical system 100 includes multiple robot assemblies 190, a processing unit or computing device 180, and an operating surgeon console or user interface 170. The robot assemblies 190 generally include a robot base 191, and a robot arm 192 for moveably supporting an end effector, robotic surgical instrument, or tool 1020 which is configured to act on tissue of a patient 104 at a surgical site "S." The ends of each of the arms 192 may include an imaging device 56 for imaging the surgical site "S," and/or a tool detection system (not shown) that identifies the tool 1020 (e.g., a type of surgical instrument) supported or attached to the end of the arm 192.

The processing unit 180 electrically interconnects the robot assemblies 190 and the surgeon console 170 to process and/or send signals transmitted and/or received between the surgeon console 170 and the robot system 190, as described in further detail below.

The surgeon console 170 includes a display device 122 which is configured to display three-dimensional images. The display device 122 displays three-dimensional images of the surgical site "S" which may include data captured by the imaging devices 56 positioned on the ends of the arms 192 and/or include data captured by imaging devices that are positioned about the surgical theater (e.g., an imaging device 56 positioned within the surgical site "S," an imaging device positioned adjacent the patient 104, an imaging device 56 positioned at a distal end of an imaging arm). The imaging devices 56 may capture visual images, infra-red images, ultrasound images, X-ray images, thermal images, and/or any other known real-time images of the surgical site "S." The imaging devices 56 transmit captured imaging data to the processing unit 180 which creates three-dimensional images of the surgical site "S" in real-time from the imaging data and transmits the three-dimensional images to the display device 122 for display.

The surgeon console 170 includes control arms 1042 which support control arm assemblies 1046 to allow a clinician to manipulate the robot assemblies 190 (e.g., move the arms 192, the ends of the arms 192, and/or the tools 1020). The control arm assemblies 1046 are in communication with the processing unit 180 to transmit control signals thereto and to receive feedback signals therefrom which, in turn, transmit control signals to, and receive feedback signals from, the robot assemblies 190 to execute a desired movement of robot assemblies 190.

Each control arm assembly 1046 includes a gimbal 1060 operably coupled to the control arm 1042 and an input device or handle assembly 1000 (e.g., similar to handles 112A, 112B described above) operably coupled to the gimbal 1060. Each of the handle assemblies 1000 is moveable through a predefined workspace within a coordinate system having "X," "Y," and "Z" axes to move the ends of the arms 192 within a surgical site "S." As the handle assemblies 1000 are moved, the tools 1020 are moved within the surgical site "S." It should be understood that movement of the tools 1020 may also include movement of the arms 192 and/or the ends of the arms 192 which support the tools 1020.

The three-dimensional images on the display device 122 are orientated such that the movement of the gimbals 1060, as a result of the movement of the handle assemblies 1000, moves the ends of the arms 192 as viewed on the display device 122. It will be appreciated that the orientation of the three-dimensional images on the display device 122 may be mirrored or rotated relative to a view from above the patient 104. In addition, it will be appreciated that the size of the three-dimensional images on the display device 122 may be scaled to be larger or smaller than the actual structures of the surgical site "S" to permit a clinician to have a better view of structures within the surgical site "S." For a detailed discussion of scaling of handle assembly movement, reference may be made to commonly owned International Patent Application Serial No. PCT/US16/65588, the entire contents of which are incorporated herein by reference.

For a detailed discussion of the construction and operation of a robotic surgical system, reference may be made to U.S. Pat. No. 8,828,023, the entire contents of which are incorporated herein by reference.

Figure 10:
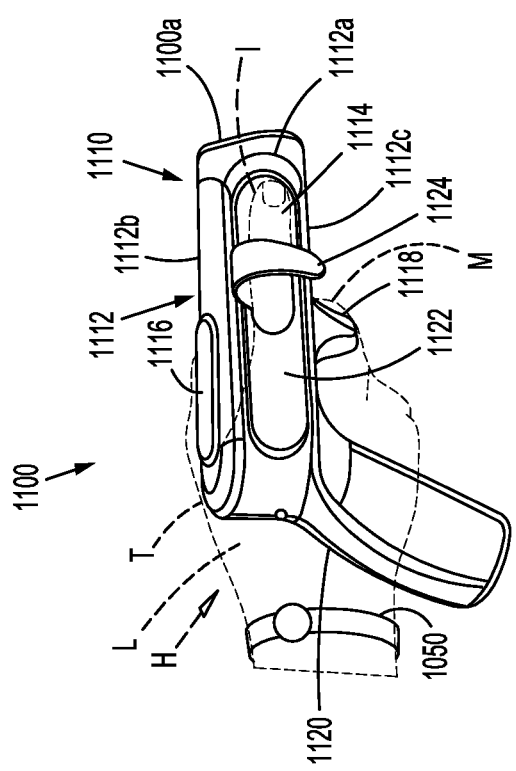
FIG. 10 is a perspective view of a handle assembly of one of the control arm assemblies of FIG. 9, with a hand of a clinician shown in phantom.

Referring now to FIG. 10, each gimbal 1060 of the control arm assemblies 1046 includes an outer link 1062, an intermediate link 1064, and an inner link 1066. The outer link 1062 includes a first end 1062a pivotably connected to the control arm 1042 and a second end 1062b pivotably connected to a first end 1064a of the intermediate link 1064 such that the intermediate link 1064 is rotatable, as indicated by arrow "$X_1$" (FIG. 9), about the "X" axis. The intermediate link 1064 includes a second end 1064b pivotably connected to a first end 1066a of the inner link 1066 such that the inner link 1066 is rotatable, as indicated by arrow "$Y_1$" (FIG. 9), about the "Y" axis. The inner link 1066 includes a second end 1066b having a connector 1068 configured to releasably engage a distal end portion 1000a of the handle assembly 1000 such that the handle assembly 1000 is rotatable, as indicated by arrow "$Z_1$" (FIG. 9), about the "Z" axis.

In embodiments, the outer, intermediate, and inner links 1062, 1064, 1066 are each substantially L-shaped frames that are configured to nest within each other. However, it should be understood that the outer, intermediate, and inner links 1062, 1064, 1066 may be any shape so long as the "X," "Y," and "Z" axes are orthogonal to each other in the zero or home position (see e.g., FIG. 10). It should also be understood that other gimbal configurations may be utilized in the control arm assemblies 1046 so long as the movement of the handle assemblies 1000 about the "X," "Y," and "Z" axes is maintained. Further still, the connector 1068 of the gimbal 1060 may allow for different sized or kinds of handle assemblies 1000 to be used to control the arms 192 and/or the tools 1020 of the robot assemblies 190.

Figure 11:
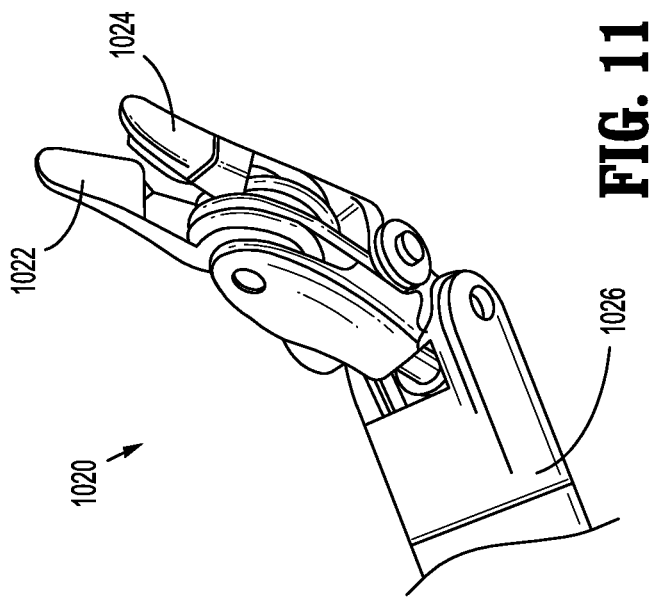
FIG. 11 is a perspective view of a tool of the robotic surgical system of FIG. 8.

As shown in FIGS. 10 and 11, the handle assembly 1000 of each of the control arm assemblies 1046 includes a body portion 1110 and a grip portion 1120. The body portion 1110 includes a housing 1112 supporting a plurality of actuators 1114, 1116, 1118 for controlling various functions of the tool 1020 (FIG. 9) of the robot assemblies 190. As illustrated and oriented in FIG. 11, the first actuator 1114 is disposed on an outer side surface 1112a of the housing 1112 in the form of a paddle, the second actuator 1116 is disposed on a top surface 1112b of the housing 1112 in the form of a button, and the third actuator 1118 extends from a bottom surface 1112c of the housing 1112 in the form of a trigger. It should be understood that the first, second, and third actuators 1114, 1116, 1118 can have any suitable configuration (e.g., buttons, knobs, paddles, toggles, slides, triggers, rockers, etc.), and number of and placement of the first, second, and third actuators 1114, 1116, 1118 about the handle assembly 1000 may vary. The first actuator 1114 includes a finger rest 1122 and a strap 1124 extending over the finger rest 1122 to secure a finger (e.g., the index finger "I") of the clinician's hand to the first actuator 1114 so that the handle assembly 1000 does not slide relative to the finger.

With continued reference to FIG. 11, the handle assembly 1000 is gripped by a surgeon or clinician such that the index finger "I" (shown in phantom) of the clinician's hand "H" rests upon the first actuator 1114, the palm "L" of the clinician's hand "H" rests on the body and grip portions 1110, 1120 of the handle assembly 1000, and the thumb "T" and the middle finger "M" of the clinician's hand "H" are free to actuate the second and third actuators 1116, 1118, respectively.

Figure 12:
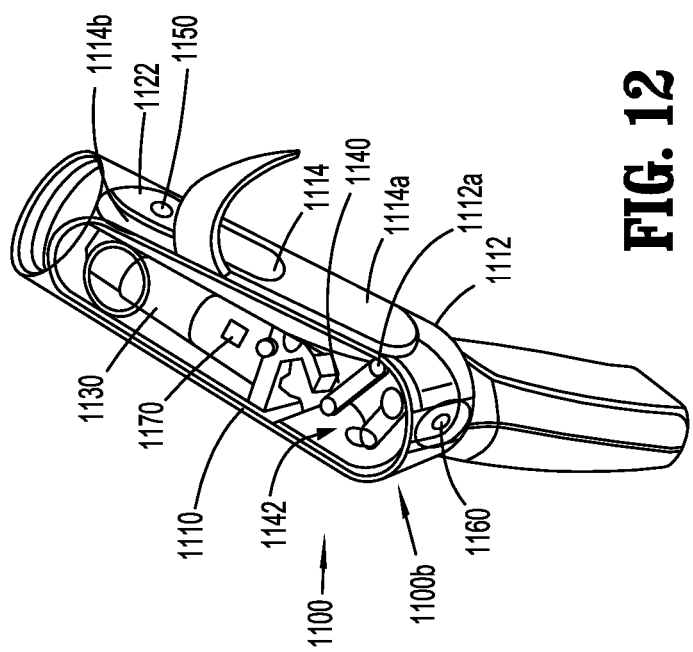

Each handle assembly 1000 allows a clinician to manipulate (e.g., clamp, grasp, fire, open, close, rotate, thrust, slice, etc.) the respective tool 1020 supported at the end of the arm 192 (FIG. 9). As shown, for example, in FIG. 12, the tool 1020 may be a jaw assembly including opposed jaw members 1022, 1024 extending from a tool shaft 1026. The first actuator 1114 may be configured to actuate the jaw members 1022, 1024 of the tool 1020 between open and closed configurations. The second and third actuators 1116, 1118 effect other functions of the tool 1020, such as fixing the configuration of the jaw members 1022, 1024 relative to one another, rotating the jaw members 1022, 1024 relative to the tool shaft 1026, firing a fastener (not shown) from one of the jaw members 1022, 1024, actuating a knife (not shown) disposed within one of the jaw members 1022, 1024, activating a source of electrosurgical energy such that electrosurgical energy is delivered to tissue via the jaw members 1022, 1024, among other functions within the purview of those skilled in the art.

Figure 13:
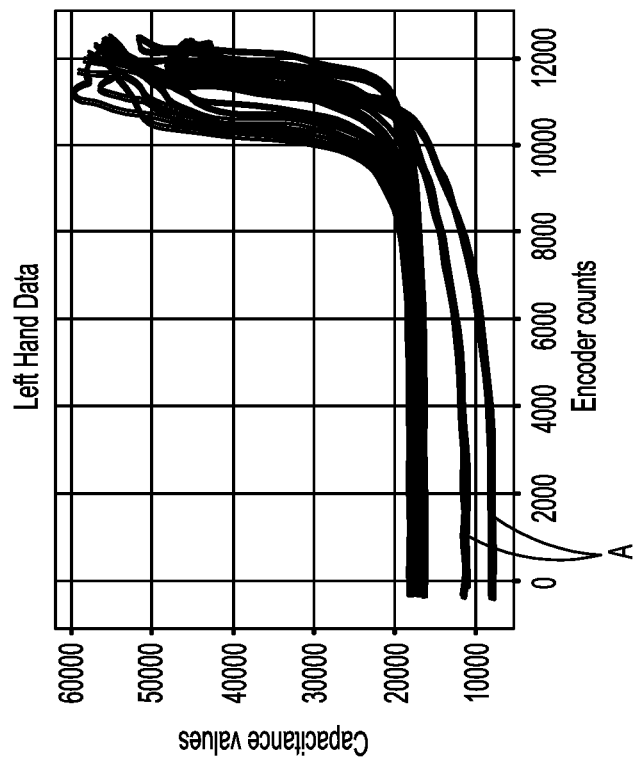

As shown in FIG. 13, a controller 1130 is disposed within the body portion 1110 of the handle assembly 1000 such that actuation of the first, second, and/or third actuator 1114, 1116, 1118 (FIG. 11) actuates the controller 1130 which converts mechanical movement of the first, second, and/or third actuators 1114, 1116, 1118 into electrical signals for processing by the processing unit 180 (FIG. 9) which, in turn, sends electrical signals to the robot assemblies 190 (FIG. 9) to actuate a function of the tool 1020 (FIG. 9). It should be understood that the robot assemblies 190 may send signals to the computing device 180 and thus, to the controller 1130 to provide feedback to a clinician operating the handle assembly 1000.

The first actuator 1214 is mechanically coupled to the controller 1130 by a linkage assembly 1140 including a four-bar linkage 1142 and a gear (not shown) rotatable upon movement of the four-bar linkage 1142. Actuation of the first actuator 1114 causes mechanical movement of a component of the controller 1130 which is converted by the controller 1130 into an electrical signal. For a detailed discussion of the construction and operation of the four-bar linkage assembly, reference may be made to International Patent Appl. Ser. No. PCT/US2017/035583, the entire content of which is incorporated herein by reference.

The first actuator 1114 includes a proximal portion 1114a and a distal portion 1114b including the finger rest 1122. The first actuator 1114 has a biased or open position, when no force is applied to the first actuator 1114, where the distal portion 1114b extends laterally from the outer side surface 1112a of the housing 1112 of the handle assembly 1000 and the proximal portion 1114a is flush with, or is disposed within, the outer side surface 1112a, as shown in FIG. 13.

In use, when a clinician presses on and applies force to the finger rest 1122, the first actuator 1114 is moved to an actuated or closed position where the distal portion 1114b of the first actuator 1114 moves towards the body portion 1110 of the handle assembly 1000 causing the proximal portion 1114a of the first actuator 1114 to move laterally away from the body portion 1110, resulting in a corresponding movement of the linkage assembly 1140. The four-bar linkage 1142 act as a crank for rotating the gear (not shown) of the linkage assembly 1140 which is meshingly engaged with a gear (not shown) of the controller 1130 such that rotation of the gear of the linkage assembly 1140 causes a corresponding rotation of the gear of the controller 1130. The controller 1130 then converts mechanical movement of the gear into electronic signals including digital position and motion information that are transmitted to the processing unit 180 (FIG. 9), as discussed above.

The amount of force applied to the first actuator 1114 by a clinician moves the first actuator 1114 from the open position to the closed position to affect the position of the jaw members 1022, 1024 (FIG. 12) with respect to each other. In embodiments, the first actuator 1114 is configured such that in the open position, the jaw members 1022, 1024 are in a fully open position. As a force is applied to the first actuator 1114 towards the closed position, the first actuator 1114 moves the jaw members 1022, 1024 towards each other until they reach a fully closed position.

With continued reference to FIG. 13, each of the handle assemblies 1000 includes components of a hand detection system which may operate independently of other surgeon awareness monitoring systems, or in combination with other surgeon awareness monitoring systems (as described in detail below). These include a first sensor 1150, a second sensor 1160, and a third sensor 1170. The first sensor 1150 is disposed or embedded within the first actuator 1114 for sensing the presence of a finger on the first actuator 1114, the second sensor 1160 is disposed within a proximal end portion 1100b of the body portion 1110 for sensing the presence of a portion of a hand (e.g., the palm of the hand) about or on the body portion 1110, and the third sensor 1170 is coupled to or disposed within the controller 1130 for measuring the position of the first actuator 1114.

In embodiments, the first sensor 1150 is a capacitive sensor, the second sensor 1160 is an infrared sensor, and the third sensor 1170 is an encoder. The first sensor 1150 detects changes in a capacitive coupling between the first actuator 1114 and the body portion 1110 of the handle assembly 1000, the second sensor 1160 detects changes (e.g., heat or motion) in an area surrounding second sensor 1160, and the third sensor 1170 detects a position of the first actuator 1114. It should be understood that other sensors may be utilized in the handle assemblies 1000 for detecting changes in electrical properties (e.g., sensing and/or measuring the presence of objects that are conductive or have a dielectric different from the environment), detecting the proximity of objects, or detecting mechanical motion and generating signals in response to the motion, as is within the purview of those skilled in the art.

The capacitance sensed by the first sensor 1150 of the handle assembly 1000 changes when a finger is on or in contact with the first actuator 1114 and/or with movement of the first actuator 1114. The position of the first actuator 1114 is correlated with a finger on the finger rest 1112 of the first actuator 1114 such that the first sensor 1150 does not solely detect the presence or absence of a finger thereon. The capacitive coupling changes as the first actuator 1114 moves, and is strong or relatively high when the first actuator 1114 is in the closed position. Accordingly, as the first actuator 1114 approaches or is in the closed position, detecting finger presence on the first actuator 1114 becomes difficult.

Figure 14:
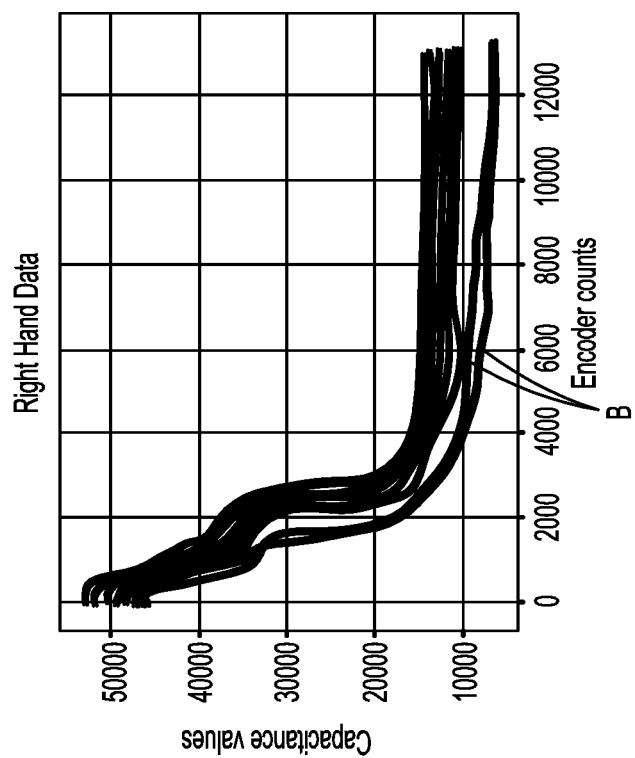
FIGS. 13 and 14 are graphs showing capacitance values as a function of encoder counts for handle assemblies of the robotic surgical system of FIG. 8, in accordance with an example of the present disclosure.
Figure 15:
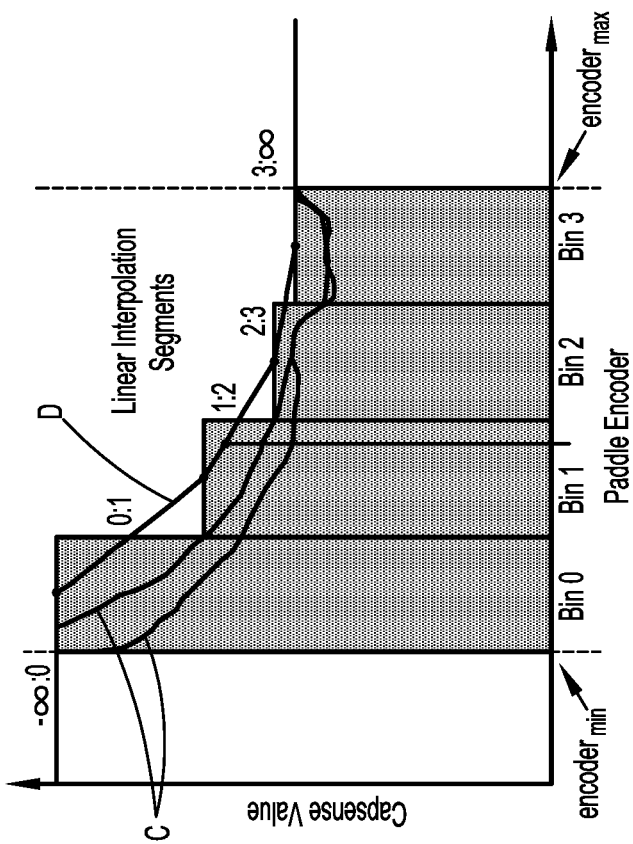
FIG. 15 is a lookup table showing capacitance values as a function of encoder counts, in accordance with an example of the present disclosure.

For example, as shown in FIGS. 14 and 15, exemplary curves illustrate capacitance values as a function of encoder counts as the position of the first actuator 1114 moves through a full range of motion between the open and closed positions. FIG. 14 shows data corresponding to the handle assembly 1000 used in the left hand of a clinician and the FIG. 15 shows data corresponding to the handle assembly 1000 used in the right hand of the clinician. The different curves in FIGS. 14 and 15 correspond to different variables during actuation of the first actuator 1114 between the open and closed positions, such as wearing and not wearing gloves, different grasps on the handle assembly 1000, etc. The two curves labeled "A" in FIG. 14 and "B" in FIG. 15 correspond to no finger being present on the first actuator 1114 during the movement between the open and closed positions. As seen in FIGS. 14 and 15, determining whether a finger is present or absent from the first actuator 1114 is difficult as the first actuator 1114 approaches the closed position and the encoder counts are high.

To detect if the clinician's hand is on the handle assembly 1000, the first sensor 1150 is utilized to not only sense the presence of a finger thereon, but to also sense the position of the first actuator 1114, and data from the first, second, and third sensors 1150, 1160, 1170 are fused or combined through a hand detection algorithm of the hand detection system. The hand detection algorithm is stored as instructions on a computer-readable medium and executed by the processing unit 180 (FIGS. 1 and 9) and/or in a processing unit (e.g., a microcontroller) of the controller 1130. The instructions, when executed by the processing unit 180, cause the hand detection system to determine if a hand is present on the handle assembly 1000 and, in turn, to send appropriate signals to the robot assemblies 190 (FIGS. 1 and 9).

The instructions (e.g., software) of the hand detection system operate during an initialization stage and an operation stage. During the initialization stage, data is recorded that captures the relationship between capacitive value, as sensed by the first sensor 1150, and the position of the first actuator 1114, as sensed by the third sensor 1170, when no hand is present on the handle assembly 1000 (e.g., no finger is on the first actuator 1114). The recorded data is then processed to construct a lookup table. During the operation stage, the lookup table is used, in conjunction with the first sensor 1150, the second sensor 1160, and the third sensor 1170, to infer hand presence or absence from the handle assembly 1000.

During the initialization stage, the response of the first sensor 1150 when no hand is present on the handle assembly 1000 is measured as a function of the position of the first actuator 1114. This measurement occurs during a calibration phase each time the operating console 170 (FIGS. 1 and 9) initializes, and accounts for the capacitive coupling between the first sensor 1150 and the handle assembly 1000, for variations between different robot surgical systems and/or components thereof, as well as for other environmental factors. During the calibration phase, the first actuator 1114 is slowly swept from the open position to the closed position (e.g., instructions are sent from the hand detection system to a paddle controller of the robotic surgical system) and the capacitive values sensed by the first sensor 1150 and the encoder counts generated by the third sensor 1170 are recorded simultaneously throughout the motion. This records baseline curves when no finger is present on the first actuator 1114 (corresponding to the black curves in FIGS. 14 and 15). The first actuator 1114 is swept in both directions (e.g., from the open position to the closed position, and back to the open position) to account for backlash in the first actuator 1114.

The data is then processed into a lookup table suitable for real-time use during a surgical procedure in order to infer finger presence on the first actuator 1114. Finger presence is inferred if the real-time capacitive value detected by the first sensor 1150 exceeds a threshold capacitive value from a calibrated curve generated by the lookup table. The lookup table is designed to enable low-latency access for use in detecting a finger on the first actuator 1114.

An illustrative lookup table is shown in FIG. 16. The lookup table is parameterized by N, a number of bins, and $encoder_{min}$ and $encoder_{max}$, which represent a range of encoder values represented by the lookup table. The width $W_{bin}$ of each bin is:

$$W_{bin} = \frac{encoder_{max} - encoder_{min}}{N}$$

Each bin covers a range of encoder values:

$$bin_i: [encode_{min} + W_{bin} i, encode_{min} + W_{bin}(i+1)]$$

As seen in the lookup table, the bins are shown as rectangles and the baseline curves labeled "C" represent example sensing data (e.g., capacitive values) recorded while sweeping the first actuator 1114 during the calibration phase. The calibrated curve labeled "D" denotes the interpolated values that would result from looking up the threshold capacitive value in the lookup table, and are labeled with the bin indicies they fall between.

To construct the lookup table, each point in the recorded data is sorted into the appropriate bin by its encoder count. The threshold capacitive value of the bin is then chosen to be the maximum capacitive value of these points and an error is thrown if there are no points in the bin. The maximum capacitive value is chosen as the threshold capacitive value to decrease the likelihood of falsely detecting a finger on the first actuator 1114 when no finger is present.

Once the lookup table is constructed, it can be queried for a capacitive value given an encoder count using linear segments that interpolate between the centers of consecutive bins (see e.g., line "D" in FIG. 16). Given an encoder count, the appropriate pair of consecutive bins is found and an interpolated value is computed. This is a fast constant-time operation by design, as this operation is used in a real-time loop. When querying with an encoder count less than $encoder_{min}$ or greater than $encoder_{max}$, the capacitive value of the first or last bin, respectively, is used.

After the initialization stage, the operation stage begins and continues to process while the robotic surgical system 100 remains in use mode. During operation of the handle assembly 1000, the lookup table is used, as described above, in conjunction with the first, second, and third sensors 1150, 1160, 1170, to infer hand presence or absence on the handle assembly 1000.

Hand presence is inferred using a combination of finger presence on the first sensor 1150 (e.g., on the first actuator 1114 of the handle assembly 1000) and the position of the first actuator 1114 as measured by the third sensor 1170, and palm presence on the second sensor 1160 (e.g., over the proximal end portion 1100a of the handle assembly 1000). In an embodiment, hand presence may be more accurately inferred by supplementing the data received from the first sensor 1150, the first actuator 1114 and the second sensor 1160 together with data received from tracking device 160 (described above).

To detect finger presence, the first sensor 1150 is used in conjunction with third sensor 1170. If the first actuator 1114 is mostly closed (e.g., the encoder count is beyond a certain threshold), then a finger is assumed to be present regardless of the real-time capacitive value sensed by the first sensor 1150. This assumption is based, for example, on the fact that the first actuator 1114 is biased to spring open without a finger holding it (e.g., due to an applied outward paddle spring torque). Such an assumption allows the real-time capacitive value to be ignored in the challenging regime where differentiating the presence versus absence of a finger is difficult (e.g., when the encoder count is high). Otherwise, if the first actuator 1114 is not closed or mostly closed (e.g., the first actuator 1114 is moved less than about 70% of the way towards the closed position), a real-time capacitive value is obtained and compared to the threshold capacitive value (corresponding to no finger) via the lookup table. If the real-time capacitive value exceeds this threshold capacitive value, then presence of a finger on the first actuator 1114 is inferred. Otherwise, the finger is deduced to be absent from the handle assembly 1000.

To detect palm presence, the real-time value (e.g., infrared value) of the second sensor 1160 is obtained and checked against a threshold value corresponding to a palm positioned about the handle assembly 1000. Palm presence or absence is deduced by checking if the real-time value exceeds the threshold value.

Finally, the finger presence state and the palm presence state are combined to determine a hand presence state (whether or not a hand is present on the handle assembly 1000). The hand presence state utilizes a "two in, two out" rule. A positive detection for each of finger presence and palm presence are necessary to transition from a negative to a positive hand presence state. A negative detection for each of finger presence and palm presence are necessary to transition from a positive to a negative hand presence state. Otherwise, no change is made from the standing positive or negative hand presence state. When the hand detection system is in a positive hand presence state, movement of the handle assemblies 1000 will cause a corresponding movement in the robot assemblies 190, and when the hand detection system is in a negative hand presence state, the robot assemblies 190 will not move (e.g., be locked) when the handle assemblies 1000 are moved.

The hand detection system will also raise exceptions under certain circumstances. For example, the instructions will raise an exception when an insufficient amount of data is used in constructing a lookup table, the data is invalid (e.g., mismatched length of encoder and capacitive sensing values) and/or there is no data corresponding to one or more bins in the lookup table.

The hand detection system may also run tests on the lookup table. Tests may verify that the lookup table correctly interpolates between values based on the data it is provided, that an error is thrown if there is no data within one or more bins of the lookup table, proper operation of the hand detection algorithm, and/or that the hand presence detector behaves properly. For example, a test may generate artificial data resembling actual capacitive sensing data for a hand of a clinician and construct a lookup table for hand detection. Various values of infrared data, capacitive values, and encoder positions are passed in to verify that the "two in, two out" rule is followed (e.g., that both the detection of a finger (via capacitive value and/or encoder count) and detection of a palm (via infrared value) are required to transition to a positive hand presence state, and the detection of no finger and no palm are required to transition to a negative hand presence state), and/or that the system correctly accounts for the case when the first actuator 1114 is closed (or mostly closed) and uses the position of the first actuator 1114 to detect the presence of a finger.

According to another aspect of the disclosure, due to the open-console architecture of the robotic surgical system 100, increased awareness around the surgeon console 170 may be achieved in relation to the area immediately surrounding the surgeon console 170 and areas further away from the surgeon console. For example, and not limited thereto, the robotic surgical system 100 may include head tracking of the surgeon for controlling a camera or endoscope within the surgical site of the patient; head tracking or gesture recognition of the surgeon for autostereoscopic display; improved eye tracking and gaze detection for identifying critical structures; situational awareness of the surgeon and operating team members near the surgeon console 170; use of special glasses with different marker patterns for distinguishing the level of expertise of the wearer (e.g. novice vs expert); autodetection of training mode; changing system parameters for users or individuals wearing glasses having markers for a novice designation; and use of wireless identification technology (e.g., radio-frequency identification or RFID) in a bracelet or ring that is worn by the user or surgeon to recognize engagement by the user or surgeon with the surgeon console 170.

In a robotic surgical system 100, having an open-console architecture, as described above, systems and algorithms may be implemented to track the head of the surgeon via the markers 164a-164e of the eyewear 163 (see FIG. 1C) for controlling the imaging devices 56 positioned on the ends of the arms 192 (e.g., camera or endoscope) that is located within the surgical site "S" of the patient itself and/or in the image captured by the imaging device 56. For example, the image capture devices 161 of the tracking device 160 may monitor and track the markers 164a-164e of the eyewear 163 worn by the surgeon and then apply algorithms or computation to determine the type of movement of the markers 164a-164e being observed by the image capture devices 161 of the tracking device 160. Depending on the type of movement or gesture observed, e.g., tilting of the head of the surgeon from side-to-side or front-to-back, pivoting of the head of the surgeon about the neck, and/or distance of the head of the surgeon from the image capture devices 161 of the tracking device 160, the computing device 180 will transform that information (independently or upon prompting by the surgeon) to effectuate a change in the imaging devices 56 positioned on the ends of the arms 192 itself and/or in the image captured by the imaging device 56. For example, the computing device 180 may command the arm 192 and/or the imaging device(s) 56 to vary a depth of insertion, vary an optical zooming scale of the image zoom, and/or roll/pitch/yaw of the imaging device(s) 56 and/or the images captured thereof.

It is further contemplated that the movement or gestures of the head of the surgeon that are observed or tracked by the tracking device 160 may be used to control other advanced features of the robotic surgical system 100 other than just the imagining device 56. For example, the movement or gestures of the head of the surgeon that are observed or tracked by the tracking device 160 may be used communicate commands to the robotic surgical system 100 to transmit controls to the arms 192, and more specifically to the instrument drive unit 194 and/or to the tool or instrument 1020 to control movement of the instrument 1020 (e.g., forceps, graspers, staplers, clip appliers, energy delivery devices, etc.).

It is contemplated that in addition to or in lieu of tracking markers 164a-164e, that an autostereoscopic display may be used to emit white light and/or infrared light onto the face of a surgeon located at the surgeon console 170, as well as for individuals in relative close proximity to the surgeon console 170. The reflection of the white light and/or infrared light off of the surgeon, and/or other individuals, may be tracked, monitored and/or recorded and analyzed using advanced computer algorithms (e.g., artificial intelligence or machine learning) to perform facial recognition on the surgeon and/or other individuals. In this manner, the facial recognition information may be used to identify the surgeon and/or individuals as experts or novices and automatically adjust performance characteristics of the robotic surgical system 100 accordingly. Still further, the facial recognition information may be supplemented with or combined with the detection of the hand of the surgeon by the input device or handle assembly 1000, to determine an awareness of the surgeon and/or individuals located at and/or around the surgeon console 170.

It is further contemplated that the robotic surgical system 100 may be configured to better track the eyes or the gaze of a surgeon wearing eyewear 163 having markers 164a-164e. As mentioned above, tracking device 160 is configured to monitor and track the location and orientation of the markers 164a-164e, and may also track the direction of the location and/or orientation of the eyes or gaze of the eyes of the surgeon. Specifically, the data captured by the image capture devices 161 of tracking device 160 in regards to the markers 164a-164e of eyewear 163 may be supplemented with data regarding the direction of gaze of the eyes of the surgeon. In this manner, the computing device 180 can calculate an angular orientation of a plane defined by the markers 164a-164e of eyewear 163 and also calculate an axis for the line of sight of the gaze of the surgeon extending through the plane defined by the markers 164a-164e of eyewear 163. These two reference geometries (e.g., the plane defined by the markers 164a-164e of eyewear 163, and the axis of the line of sight of the gaze of the surgeon) may be used by the computing device 180 to highlight or identify zones of interest on the display 122 with increased accuracy. The axis for the line of sight of the gaze of the surgeon may be estimated to the imaginary line 207 (normal to the plane defined by the markers 164a-164e, as described above), or may be more accurately determined by monitoring and tracking the eyes of the surgeon and therefore my not necessary by normal to the plane defined by the markers 164a-164e.

As mentioned above, in accordance with the present disclosure, the robotic surgical system 100 includes improved situational awareness of the surgeon and operating team members near the surgeon console 170. Specifically, the image capture devices 161 of tracking device 160 may capture images in any direction around the surgeon console, and not only limited to a direction oriented toward the surgeon. These images can be displayed on display 122 for the surgeon, and near-by operating team members, to observe. For example, the robotic surgical system 100 can track the numbers of sets of markers 164a-164e of eyewear 163 to determine location and movement of individuals around the surgeon console, as well as the number of individuals located around the surgeon console 170. Further, the robotic surgical system 100 can used advanced algorithms or artificial intelligence to perform facial recognition to also determine location and movement of individuals around the surgeon console, as well as the number of individuals located around the surgeon console. In this manner, the robotic surgical system 100 is monitoring and aware of the situation surrounding the surgeon console 170, and the surgeon may also be made aware, by the robotic surgical system 100, about the situations surrounding the surgeon console 170.

In a further aspect of the disclosure, the robotic surgical system 100 may be configured such that tracking device 160 is tuned or programmed to identify and track multiple sets of eyewear 163, each having the same pattern of markers 164a-164e or a different pattern of markers 164a-164e. Specifically, in an example, each marker 164a-164e may have a common pattern/shape/color and may be arranged in a common distance relative to one another. These specific details may be registered in computing device 180 and monitored or tracked by tracking device 160. Since these specific characteristics of markers 164a-164e are fixed and known, computing device 180 and/or tracking device 160 is better able to track and eyewear 163 and perform calculations more efficiently and accurately. It is contemplated that eyewear 163 may be available in various sizes corresponding the size eyewear that a specific wearer may desire/require. However, the markers 164a-164e provided on different sized eyewear may have the same specific characteristics as one another. Stated differently, for example, the specific locations of or relative distance between markers 164a-164e on relatively small eyewear 163 may the same for relatively large eyewear 163.

In a further, slightly different embodiment, eyewear 163 may be provided with different markers 164a-164e from one another. For example, eyewear 163 that is worn by the surgeon (e.g., "expert" or master) may have one discrete set of markers 164a-164e, while eyewear 163 worn by an operating room clinician, a more novice surgeon, or a student (e.g., "novice" or slave) may have a different set of markers 164a-164e. In this manner, the robotic surgical system 100 may be configured such that the tracking device 160 is tuned or programmed to monitor and track these differences in the patterns/characteristics of the markers 164a-164e, and modify the performance characteristics of any aspect of the robotic surgical system 100.

For example, if the tracking device 160 identifies the presence of an expert surgeon seated at the surgeon console 170, then the robotic surgical system 100 may enable full functionality of all the features thereof and/or appropriately set certain parameters, features to particular levels, such as, for example, setting specific scaling factors, speed limits, force limits, force feedback limits and/or other advanced artificial intelligence features (e.g., facial recognition, gesture recognition, etc.). However, if the tracking device 160 identifies the presence of a novice surgeon or student seated at the surgeon console 170, then the robotic surgical system 100 may disable certain functionality of some features thereof and/or appropriately set at least the aforementioned parameters or features of the robotic surgical system 100 mentioned above. In a specific example, if the tracking device 160 identifies the presence of a specific particular pattern of markers 164a-164e for eyewear 163, which corresponds to a novice surgeon or student being seated at the surgeon console 170, then the robotic surgical system 100 may automatically enter into a training mode, and, for example, prompt the user to go through various training modules or the like.

Further, if the tracking device 160 identifies the presence of both an expert and a novice surgeon located in close proximity to the surgeon console 170, then the robotic surgical system 100 may enable full functionality of all the features thereof and/or appropriately set certain features to particular levels, or some other predesignated setting.

It is still further envisioned that the robotic surgical system 100 may be configured to calculate the proximity of any sets of markers 164a-164e relative to the surgeon console 170 and/or to the tracking device 160, to optionally activate or deactivate certain features of the robotic surgical system 100. In an embodiment, if the tracking device 160 detects the presence of two or more sets of eyewear 163, the robotic surgical system 100 may provide control to or receive control from the eyewear 163 which is calculated to be located between input device or handle assembly 1000 or the eyewear 163 that is located in closest proximity to input device or handle assembly 1000.

In accordance with the present disclosure, as mentioned briefly above, it is further envisioned that the robotic surgical system 100 may be provided with wireless identification technology (e.g., radio-frequency identification or RFID) in a bracelet 1050 (see FIG. 11) or ring that is worn by the user or surgeon to recognize engagement by the user or surgeon with the surgeon console 170. The wireless identification technology may function in collaboration with or in place of the above-mentioned hand detection features (e.g., capacitive, infrared and/or position sensors) to determine that the hand of the surgeon is engaged with input device or handle assembly 1000, or other awareness parameters for the user.

The wireless identification device may include identification information related to the user; robotic surgical system performance characteristic associated with the user (e.g., parameters which the surgeon prefers for operation and/or control of the robotic surgical system, such as, for example, scaling factors, force feedback factors, performance or input response factors, etc.); and/or proximity information of the wireless identification device relative to the surgeon console and/or the handle assembly.

In addition to RFID communication, it is contemplated that any form of communication may be used for bracelet 1050, such as, for example, and not limited to, optical, WIFI, Bluetooth® (an open wireless protocol for exchanging data over short distances (using short length radio waves) from fixed and mobile devices, creating personal area networks (PANs)), ZigBee® (a specification for a suite of high level communication protocols using small, low-power digital radios based on the IEEE 802.15.4-2003 standard for wireless personal area networks (WPANs)), Near-field communication, etc.

In accordance with the present disclosure, the tracking of the eyewear 163, as described in any of the embodiments above, may be combined with the detection of the hand of the surgeon by the input device or handle assembly 1000, as described in any of the embodiments above, in order to supplement the surgeon attention monitoring of the robotic surgical system 100. Specifically, the tracking of the markers 164a-164e of the eyewear 163 is scored and provided with a head tracking value, the detection of the hand of the surgeon in a first input device 1000, e.g., a right-side input device, is scored and provided with a first hand value, and the detection of the hand of the surgeon in a second input device 1000, e.g., a left-side input device, is scored and provided with a second hand value. These three values are all monitored and algorithms applied thereto to determine the level of attention of the surgeon taking place with the robotic surgical system 100.

In a mode of implementation, the robotic surgical system 100 may only operate in a fully functional state when each of the values is determined to be above a certain predetermined threshold value. In another mode of operation, the robotic surgical system 100 may only operate in a fully functional state when two of the three values is determined to be above a certain predetermined threshold value, or the robotic surgical system 100 may operate in a less than fully functional state when two of the three values is determined to be above a certain predetermined threshold value.

In a further mode of operation, the robotic surgical system 100 may operate in the fully functional state or some other predetermined state when it is observed or determined that the head tracking value is above a predetermined threshold value, and one of the first hand value and the second hand value is above a predetermined threshold value. In this manner, the robotic surgical system 100 may still operate is some functional state when the surgeon releases one of the ride side input device 1000 and the left side input device 1000. This permits the surgeon to physically point to images on display 122 for instruction or teaching purposes, or to interact with other input controls of the surgeon console 170 (e.g., touch screen controller, etc.). However, if it is observed or determined that the head tracking value is below a predetermined threshold value, and only one of the first hand value and the second hand value is above a predetermined threshold value, then the robotic surgical system 100 may only operate is some functional state which is less than the fully functional state.

The phrases "in an example," "in examples," "in some examples," "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory described herein. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A robotic surgical system with user engagement monitoring, comprising:
   a robot assembly including a robotic arm coupled to a surgical instrument;
   a surgeon console including:
      a handle assembly communicatively coupled to at least one of the robot assembly, the robotic arm, or the surgical instrument, the handle assembly including a body portion having a proximal end portion and a distal end portion, the body portion including a first actuator movable between an open position and a closed position;
      a hand detection system including a first sensor disposed within the first actuator of the handle assembly for detecting finger presence on the first actuator, a second sensor disposed on the proximal end portion of the handle assembly for detecting palm presence about the proximal end portion, and a third sensor disposed within the body portion of the handle assembly for detecting position of the first actuator relative to the body portion;
a display device; and
a processing unit electrically coupled to the first, second, and third sensors for receiving and processing data from the first, second, and third sensors;
a tracking device including an image capture device configured to capture an image of a user position reference point; and
a computing device,
wherein at least one of the surgeon console, the hand detection system or the tracking device is configured to:
compute, based on the captured image, a position of the user position reference point relative to the display device,
determine whether a user is engaged with or disengaged from the surgeon console based on the computed position,
determine whether a hand of the user is engaged with or disengaged from at least one of the first, second or third sensors of the hand detection system, and
in response to a determination that the user is disengaged from the surgeon console or the hand of the user is disengaged from at least one of the first, second or third sensors of the hand detection system, cause the robotic surgical system to operate in a safe mode,
wherein at least one of the surgeon console, the hand detection system or the tracking device is further configured to, at a time when the robotic surgical system operates in the safe mode:
restrict movement of the handle assembly from a previous position of the handle assembly, and
transmit, to the computing device, instructions to restrict movement of at least one of the robot assembly, the robotic arm, or the surgical instrument;
wherein the computing device is configured to:
receive the instructions, and
transmit the instructions to the at least one of the robot assembly, the robotic arm, or the surgical instrument; and
wherein at least one of the robotic arm, the robot assembly, or the surgical instrument is configured to:
receive the instructions, and
restrict movement of at least one of the robot assembly, the robotic arm, or the surgical instrument in response to the instructions.

2. The robotic surgical system according to claim 1, wherein at least one of the surgeon console, the hand detection system or the tracking device is further configured to compute the position of the user position reference point by generating location data corresponding to at least one of the position, or an orientation, of the user position reference point, within a three-dimensional coordinate space, relative to the display device.

3. The robotic surgical system according to claim 1, wherein at least one of the surgeon console, the hand detection system or the tracking device is further configured to, at a time when the robotic surgical system operates in the safe mode:
in response to a determination that the user is engaged with the surgeon console by at least one of the tracking device or the hand detection system, cause the robotic surgical system to exit the safe mode after an elapsing of a threshold amount of time after the determination that the user is engaged.

4. The robotic surgical system according to claim 1, wherein at least one of the surgeon console, the hand detection system or the tracking device is further configured to, at a time when the robotic surgical system operates in the safe mode:
prevent a movement of the handle assembly from causing a corresponding movement of the robotic arm communicatively coupled to the handle assembly.

5. The robotic surgical system according to claim 1, wherein at least one of the surgeon console, the hand detection system or the tracking device is further configured to:
detect an amount of movement of the handle assembly;
determine, based on the amount of movement of the handle assembly, an amount of movement of at least one of the robot assembly, the robotic arm, or the surgical instrument to be caused in response to the movement of the handle assembly; and
cause at least one of the robot assembly, the robotic arm, or the surgical instrument to move by the determined amount of movement,
wherein, at a time when the robotic surgical system operates in the safe mode, the determination of the amount of movement of at least one of the robot assembly, the robotic arm, or the surgical instrument to be caused includes applying a downward scaling factor.

6. The robotic surgical system according to claim 5, wherein at least one of the surgeon console, the hand detection system or the tracking device is further configured to:
compute a velocity of a movement of the handle assembly; and
modify the downward scaling factor based on the velocity.

7. A robotic surgical system with user engagement monitoring, comprising:
a robot assembly including a robotic arm coupled to a surgical instrument;
a surgeon console including:
a handle assembly communicatively coupled to at least one of the robot assembly, the robotic arm, or the surgical instrument, the handle assembly including a body portion having a proximal end portion and a distal end portion, the body portion including a first actuator movable between an open position and a closed position;
a hand detection system including a first sensor disposed within the first actuator of the handle assembly for detecting finger presence on the first actuator, a second sensor disposed on the proximal end portion of the handle assembly for detecting palm presence about the proximal end portion, a third sensor disposed within the body portion of the handle assembly for detecting position of the first actuator relative to the body portion;
a display device; and
a processing unit electrically coupled to the first, second, and third sensors for receiving and processing data from the first, second, and third sensors;
a tracking device including an image capture device configured to capture an image of a user position reference point,
wherein at least one of the surgeon console, the hand detection system or the tracking device is configured to:
compute, based on the captured image, a position of the user position reference point relative to the display device, determine whether a user is engaged with or disengaged from the surgeon console based on the computed position, determine whether a hand of the user is engaged with or disengaged from at least one of the first, second or third sensors of the hand detection system, and in response to a determination that the user is disengaged from the surgeon console or the hand of the user is disengaged from at least one of the first, second or third sensors of the hand detection system, cause the robotic surgical system to operate in a safe mode; and a plurality of eyewear each including a discrete plurality of markers, wherein a first user position reference point includes first data from a first plurality of markers of first eyewear corresponding to the user, and a second user positioning reference point including second data from a second plurality of markers of second eyewear, different from the first data, corresponding to a non-user.

8. The robotic surgical system according to claim 1, wherein the first sensor is a capacitive sensor, the second sensor is an infrared sensor, and the third sensor is an encoder.

9. A robotic surgical system with user engagement monitoring, comprising:
a robot assembly including a robotic arm coupled to a surgical instrument;
a surgeon console including:
a handle assembly communicatively coupled to at least one of the robot assembly, the robotic arm, or the surgical instrument, the handle assembly including a body portion having a proximal end portion and a distal end portion, the body portion including a first actuator movable between an open position and a closed position;
a hand detection system including a first sensor disposed within the first actuator of the handle assembly for detecting finger presence on the first actuator, a second sensor disposed on the proximal end portion of the handle assembly for detecting palm presence about the proximal end portion, and a third sensor disposed within the body portion of the handle assembly for detecting position of the first actuator relative to the body portion;
a display device; and
a processing unit electrically coupled to the first, second, and third sensors for receiving and processing data from the first, second, and third sensors; and
a tracking device including an image capture device configured to capture an image of a user position reference point,
wherein at least one of the surgeon console, the hand detection system or the tracking device is configured to:
compute, based on the captured image, a position of the user position reference point relative to the display device,
determine whether a user is engaged with or disengaged from the surgeon console based on the computed position,
determine whether a hand of the user is engaged with or disengaged from at least one of the first, second or third sensors of the hand detection system, and
in response to a determination that the user is disengaged from the surgeon console or the hand of the user is disengaged from at least one of the first, second or third sensors of the hand detection system, cause the robotic surgical system to operate in a safe mode, and wherein, when the hand detection system is in an initialization state, the hand detection system utilizes data from only the first and third sensors, and when the hand detection system is in an operation stage, the hand detection system utilizes data from the first, second, and third sensors.

10. The robotic surgical system according to claim 1, wherein, when the hand detection system is in an initialization stage, the first actuator moves through a full range of motion between the open and closed positions, and the first sensor detects a capacitance value at each of a plurality of points through the full range of motion and the third sensor generates an encoder count at each of the plurality of points.

11. The robotic surgical system according to claim 10 wherein the hand detection system includes a lookup table including a baseline curve of the capacitance values as a function of the encoder counts and a calibrated curve of threshold capacitance values as a function of the encoder counts.

12. The robotic surgical system according to claim 1, wherein, when the hand detection system is in an operation stage, the first sensor detects a real-time capacitance value and the third sensor detects a real-time encoder count, and the real-time capacitance value and the real-time encoder count are compared to the lookup table to identify a positive or negative finger presence state of the handle assembly.

13. The robotic surgical system according to claim 1, wherein, when the hand detection system is in an operation stage, the second sensor detects a real-time value which is compared to a threshold value to identify a positive or negative palm presence state of the handle assembly.

14. The robotic surgical system according to claim 1, wherein the surgical instrument is a jaw assembly including opposed jaw members, and when the first actuator is in the open position, the jaw members are in an open configuration, and when the first actuator is in the closed position, the jaw members are in a closed configuration.

15. The robotic surgical system according to claim 1, wherein the tracking device monitors gestures of a head of the user and combines data regarding the head gestures with data regarding a movement of the handle assembly to effectuate control of the surgical instrument.

16. The robotic surgical system according to claim 1, wherein the surgical instrument is an endoscope.

17. The robotic surgical system according to claim 1, wherein the data regarding the head gestures monitored by the tracking system is communicated to the endoscope to control a zoom scale, roll, pitch or yaw of an image captured by the endoscope.

18. The robotic surgical system according to claim 1, further comprising a wireless identification device wearable by the user to recognize engagement by the user or surgeon with the surgeon console, the wireless identification device including at least one of:
identification information related to the user;
robotic surgical system performance characteristic associated with the user; or
proximity information of the wireless identification device relative to the surgeon console and/or the handle assembly.

19. The robotic surgical system according to claim 18, wherein the wireless identification device is used in combination with the hand detection system for determining an awareness of the user.

\* \* \* \* \*